(12) United States Patent
Nagahama

(10) Patent No.: US 10,975,117 B2
(45) Date of Patent: Apr. 13, 2021

(54) METHOD FOR PRODUCING LACOSAMIDE AND INTERMEDIATE THEREOF

(71) Applicant: API CORPORATION, Tokyo (JP)

(72) Inventor: Masaki Nagahama, Fukuoka (JP)

(73) Assignee: API CORPORATION, Tokyo (JP)

( * ) Notice: Subject to any disclaimer, the term of this patent is extended or adjusted under 35 U.S.C. 154(b) by 0 days.

(21) Appl. No.: 15/775,581

(22) PCT Filed: Nov. 11, 2016

(86) PCT No.: PCT/JP2016/083551
§ 371 (c)(1),
(2) Date: May 11, 2018

(87) PCT Pub. No.: WO2017/082396
PCT Pub. Date: May 18, 2017

(65) Prior Publication Data
US 2018/0371013 A1  Dec. 27, 2018

(30) Foreign Application Priority Data
Nov. 13, 2015 (JP) .............................. JP2015-222754

(51) Int. Cl.
| | |
|---|---|
| *C07K 5/062* | (2006.01) |
| *C07B 57/00* | (2006.01) |
| *C07C 231/12* | (2006.01) |
| *C07C 231/20* | (2006.01) |
| *A61K 31/165* | (2006.01) |
| *C07C 237/06* | (2006.01) |
| *C07C 233/47* | (2006.01) |
| *C07C 231/02* | (2006.01) |

(52) U.S. Cl.
CPC .......... *C07K 5/0606* (2013.01); *A61K 31/165* (2013.01); *C07B 57/00* (2013.01); *C07C 231/02* (2013.01); *C07C 231/12* (2013.01); *C07C 231/20* (2013.01); *C07C 233/47* (2013.01); *C07C 237/06* (2013.01)

(58) Field of Classification Search
None
See application file for complete search history.

(56) References Cited

U.S. PATENT DOCUMENTS

| | | |
|---|---|---|
| 6,048,899 A | 4/2000 | Kohn et al. |
| RE38,551 E | 7/2004 | Kohn |
| 8,093,426 B2 | 1/2012 | Madhra et al. |

FOREIGN PATENT DOCUMENTS

| | | |
|---|---|---|
| JP | 2012-508162 A | 4/2012 |
| WO | 2006/037574 A1 | 4/2006 |
| WO | 2010/052011 A1 | 5/2010 |
| WO | 2011/039781 A1 | 4/2011 |
| WO | 2011/092559 A1 | 8/2011 |
| WO | 2012/065891 A1 | 5/2012 |
| WO | 2012/069855 A1 | 5/2012 |
| WO | 2013/072933 A2 | 5/2013 |
| WO | 2014/068333 A2 | 5/2014 |
| WO | 2016/021711 A1 | 2/2016 |
| WO | 2016/039393 A1 | 3/2016 |

OTHER PUBLICATIONS

Partial Supplementary European Search Report for EP App No. 16864357.5 dated Mar. 11, 2019.
McIntyre et al., "Lacosamide", Drugs of the Future, 2004, 29 (10): 992-997.
International Search Report for PCT/JP2016/083551, dated Feb. 7, 2017.
Written Opinion for PCT/JP2016/083551, dated Feb. 7, 2017.
EESR for EP App. No. 16 86 4357.5 dated Jun. 14, 2019.
Extended European Search Report (EESR) dated Apr. 17, 2020 issued in EP Patent Application No. 20152731.4.
European Office Action dated May 15, 2020 issued in EP Patent Application No. 16864357.5.
JP Office Action issued in JP Patent Application No. 2017-550414, dated Dec. 8, 2020, English translation.
EP Office Action issued in EP Patent Application No. 16864357.5, dated Jan. 22, 2021.

*Primary Examiner* — Thomas S Heard
(74) *Attorney, Agent, or Firm* — Greenblum & Bernstein, P.L.C.

(57) ABSTRACT

The present invention provides a method of industrially and safely producing lacosamide high in diastereomeric excess at a high yield and a low cost. Adopting a particular isomerization-crystallization condition makes it possible to a method of industrially and safely producing lacosamide high in diastereomeric excess at a high yield and a low cost. Additionally, an intermediate efficacious for producing lacosamide is provided.

7 Claims, 4 Drawing Sheets

METHOD FOR PRODUCING LACOSAMIDE AND INTERMEDIATE THEREOF

FIELD

The present invention relates to a method for producing (R)—N-benzyl-2-acetylamino-3-methoxypropionamide (hereinafter sometimes referred to as "lacosamide") and a method for producing an intermediate thereof.

BACKGROUND

Lacosamide is a medicine efficacious for treatment for epilepsy and pain.

Patent Literatures 1 and 2 and Non-Patent Literature 1 each disclose a method for producing lacosamide that uses D-serine and a derivative thereof as starting material and uses methyl iodide and silver oxide as an O-methylation reagent. Patent Literature 3 discloses a method that uses dimethyl sulfate as an O-methylation reagent. Patent Literatures 4 and 5 each disclose a method that protects the amino group before methylation of the hydroxyl group.

The above methods use expensive D-serine and derivatives thereof as starting material and use expensive O-methylation reagent and protection reagent, which means a process of introducing a protection group and a process of deprotection are required. Accordingly method able to produce lacosamide inexpensively has been desired from an industrial viewpoint. In particular, the method of Patent Literature 3 uses a large amount of dimethyl sulfate for producing lacosamide in the industrial large scale, which may arise safety and/or environmental problems. Accordingly, a demand has arisen for a safe and environment-friendly method for producing lacosamide.

Patent Literatures 6, 7, and 8 disclose a method for producing lacosamide by generating a racemic lacosamide or an intermediate thereof and resolving the racemic mixture, and a method for producing lacosamide by resolving enantiomer with a Simulated Moving Bed (SMB) resolving device. Unfortunately, these methods do not achieve satisfactory result in the aspects of the yield and the diastereomeric excess, and also require unordinary resolving device.

For example, although Patent Literature 6 discloses a method for producing lacosamide by generating racemic lacosamide intermediate without using a racemizing reagent, making the intermediate react with a reagent such as N-acetyl-D-leucine, and resolving the racemic intermediate by means of forming a diastereomeric salt or by means of chiral chromatography. The reaction of forming a diastereomeric salt with N-acetyl-D-leucine is carried out at a reaction temperature as high as 85° C. and unfortunately does not achieve satisfactory yield and diastereomeric excess.

Patent Literature 9 discloses a method for producing lacosamide by generating racemic lacosamide intermediate and making the intermediate react with N-formyl-L-leucine to form a diastereomeric salt to be resolved. Unfortunately, the method is not satisfactory industrial method in the aspects of the cost and the production efficiency for preferably using a co-solvent, using a large amount of the solvent, and requiring high reaction temperature. Furthermore, as apparent from Comparative Example 1 to be described below, the method is not satisfactory in the aspects of the yield and the diastereomeric excess.

Patent Literature 10 discloses a method for producing lacosamide by stereoselectively acetylating a racemic intermediate of lacosamide by using enzyme in the presence of an aldehyde, but unfortunately is not satisfactory in the aspects of the yield and the diastereomeric excess. In addition, this method takes a long time for reaction and requires to recollect the enzyme for repetitious reuse, and is therefore not a satisfactory industrial method for producing.

As described above, the methods already known to the public do not achieve satisfactory yield and diastereomeric excess, and uses expensive material and an unordinary resolving device. A demand arises for an industrial method for producing that improves the efficiency, the cost, the safety, and the environmental impact.

PRIOR ART REFERENCE

Patent Literature

[Patent Literature 1] U.S. Reissue Pat. No. RE38551
[Patent Literature 2] U.S. Pat. No. 6,048,899
[Patent Literature 3] WO2006/037574
[Patent Literature 4] U.S. Pat. No. 8,093,426
[Patent Literature 5] WO2011/039781
[Patent Literature 6] WO2010/052011
[Patent Literature 7] WO2012/065891
[Patent Literature 8] WO2011/092559
[Patent Literature 9] WO2014/068333
[Patent Literature 10] WO2012/69855

Non-Patent Literature

[Non-Patent Literature 1] Drugs Future 2004, 29, 992-997

SUMMARY

Problems to be Solved by Invention

The object of the present invention is to provide an industrial method for safely producing lacosamide high in both diastereomeric excess and chemical purity at a high yield and at a low cost.

Means to Solve the Problem

As a result of enthusiastic development, Inventors have found that lacosamide high in both diastereomeric excess and chemical purity can be efficiently and economically produced by adopting a particular isomerization-crystallization condition and completed the present invention. In addition to the above, Inventors have also found that lacosamide can be produced further efficiently and economically by adopting a particular acetylation condition and completed the present invention.

The scopes of the present inventions are as follows:

[1] A method for producing lacosamide including: an isomerization-crystallization process that causes racemic N-benzyl-2-amino-3-methoxypropionamide to react with at least one selected from a group consisting of N-acetylamino acid and N-formylamino acid in a solvent in the presence of an aldehyde compound at a temperature lower than 65° C. to selectively crystallize a salt of R-configuration of N-benzyl-2-amino-3-methoxypropionamide and N-acetylamino acid or N-formylamino acid; and an acetylation process that acetylates the R-configuration N-benzyl-2-amino-3-methoxypropionamide contained in the salt to obtain lacosamide.

[2] The method according to above [1], wherein an amount of the solvent is 20 mL or less to the racemic N-benzyl-2-amino-3-methoxypropionamide of one gram.

[3] The method according to the above [1] or [2], wherein, in the isomerization-crystallization process, at least one selected from a group consisting of the N-acetylamino acid and the N-formylamino acid is dividedly provided.

[4] The method according to one of the above [1]-[3], wherein the acetylation process comprises: (i) causing the salt obtained through the isomerization-crystallization process with an acetylating reagent; or (ii) causing the salt obtained through the isomerization-crystallization process with an acid and causing the obtained R-configuration N-benzyl-2-amino-3-methoxypropionamide to react with the acetylating reagent.

[5] The method according to one of the above [1]-[4], further comprising, an amination process that aminates a compound expressed by a Formula (4) to obtain the racemic N-benzyl-2-amino-3-methoxypropionamide, the amination process being carried out before the isomerization-crystallization process

[Formula 1]

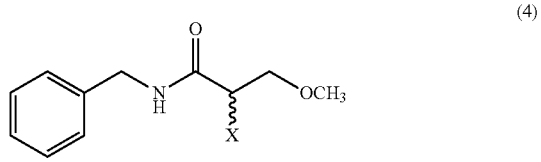

(4)

(where, the symbol X represents a leaving group).

[6] A method for producing a salt of R-configuration of N-benzyl-2-amino-3-methoxypropionamide and N-acetylamino acid or N-formylamino acid, the method including causing racemic N-benzyl-2-amino-3-methoxypropionamide to react with the one selected from a group consisting of N-acetylamino acid and N-formylamino acid in a solvent in the presence of an aldehyde compound at a temperature lower than 65° C. to selectively crystallize the salt of R-configuration of N-benzyl-2-amino-3-methoxypropionamide and N-acetylamino acid or N-formylamino acid.

[7] The method according to the above [6], wherein an amount of the solvent is 20 mL or less to the racemic N-benzyl-2-amino-3-methoxypropionamide of one gram.

[8] The method according to the above [6] or [7], wherein, in the isomerization-crystallization process, at least one selected from a group consisting of the N-acetylamino acid and the N-formylamino acid is dividedly provided.

[9] A method for producing lacosamide including causing the salt of R-configuration of N-benzyl-2-amino-3-methoxypropionamide and N-acetylamino acid to react with an acetylating reagent in a simple water solvent or an aqueous solution in a presence of a base.

[10] A method for producing lacosamide including: causing the salt of R-configuration of N-benzyl-2-amino-3-methoxypropionamide and N-acetylamino acid or N-formylamino acid to react with an acid in a solvent to separate the R-configuration of N-benzyl-2-amino-3-methoxypropionamide from N-acetylamino acid or N-formylamino acid; and causing the obtained R-configuration of N-benzyl-2-amino-3-methoxypropionamide to react with an acetylating reagent.

[11] A crystal of a salt of R-configuration of N-benzyl-2-amino-3-methoxypropionamide and N-acetylamino acid or N-formylamino acid.

[12] The crystal according to the above [11], wherein the salt of R-configuration of N-benzyl-2-amino-3-methoxypropionamide and N-acetylamine acid has a powder X-ray diffraction measuring pattern using a CuKα ray exhibiting peaks at diffraction angels (2θ±0.2°)=6° to 7.5°, 14.5° to 16°, 17.5° to 19°, and 24.5° to 26°.

[13] The crystal according to the above [11], wherein the salt of R-configuration of N-benzyl-2-amino-3-methoxypropionamide and N-formylamino acid has a powder X-ray diffraction measuring pattern using a CuKα ray exhibiting peaks at diffraction angels (2θ±0.2°)=9° to 10.5°, 11.5° to 13°, 17.5° to 19°, and 24.5° to 26°.

[14] A pharmaceutical composition including: lacosamide produced in a method defined in one of the above [1]-[5], [9], and [10]; and a vehicle pharmacologically acceptable to be mixed with the lacosamide.

Effect of Invention

The present invention can industrially and safely produce lacosamide high in diastereomeric excess and chemical purity at a high yield and a low cost, and provide an intermediate efficacious for producing lacosamide.

EMBODIMENT TO CARRY OUT INVENTION

Figure 1:
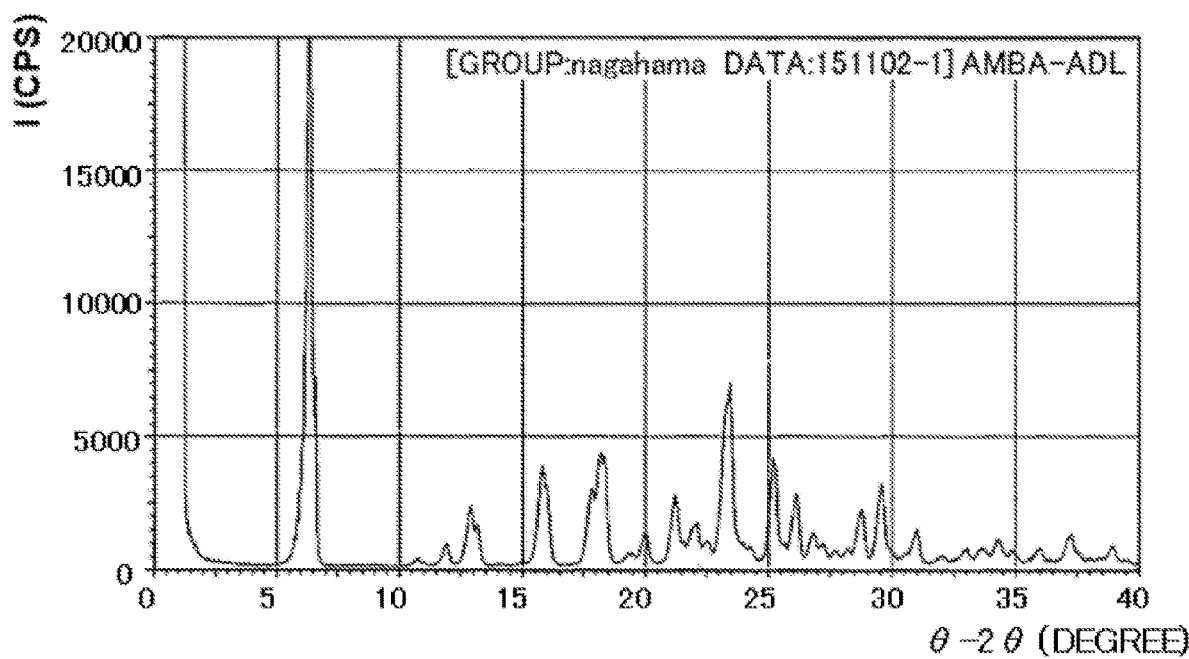
FIG. 1 is a graph plotting a powder X-ray diffraction pattern of the crystal of a salt of (R) N-benzyl-2-amino-3-methoxypropionamide and N-acetyl-D-leucine obtained in Example 1.

Hereinafter, the production method of the present invention will be described.

An embodiment of a method for producing lacosamide of the present invention involves the following scheme. Specifically, the method includes at least an isomerization-crystallization process of selectively crystallization of a salt of (R) N-benzyl-2-amino-3-methoxypropionamide and an optical resolving reagent (hereinafter also referred to as "resolving reagent") Z by causing racemic N-benzyl-2-amino-3-methoxypropionamide represented by the following formula (2) to react with the resolving reagent Z in the presence of an aldehyde compound; and an acetylation process of acetylating (R) N-benzyl-2-amino-3-methoxypropionamide in the obtained salt to obtain lacosamide represented by formula (1). The method for producing lacosamide of the present invention may further include an amination process of aminating the compound represented by the following formula (4) to obtain racemic N-benzyl-2-amino-3-methoxypropionamide. In the following scheme, the symbol X represents a leaving group and the symbol Z⁻ represents a free anion from the resolving reagent.

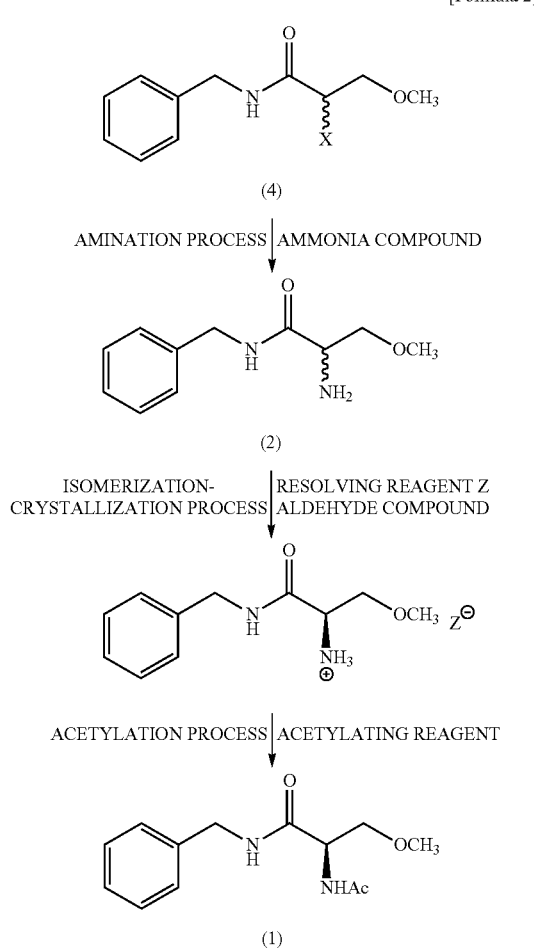

<Isomerization-Crystallization Process>

The isomerization-crystallization process of the present invention is a process that selectively crystallizes a salt of R N-benzyl-2-amino-3-methoxypropionamide and N-acetylamino acid or N-formylamino acid (hereinafter, simply referred to as a "salt") through the reaction of racemic N-benzyl-2-amino-3-methoxypropionamide (hereinafter sometimes referred to as "Compound (2)") represented by the following formula (2) with a resolving reagent of at least one selected from a group consisting of N-acetylamino acid and N-formylamino acid under the presence of an aldehyde compound in a solvent. Hereinafter, if there is no need to discriminate N-acetylamino acid and N-formylamino acid from each other, these compounds are collectively referred to as a resolving reagent in the description.

[Formula 3]

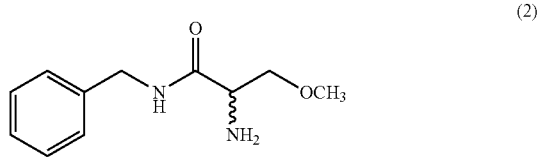

(2)

(Material)

Here, racemic N-benzyl-2-amino-3-methoxypropionamide represents a mixture of (R) N-benzyl-2-amino-3-methoxypropionamide and (S) N-benzyl-2-amino-3-methoxypropionamide. The ratio (molar ratio) between the R configuration and the S configuration is usually R:S=1 to 99:99 to 1, preferably R:S=20 to 80:80 to 20, particularly preferably R:S=40 to 60:60 to 40.

Examples of N-acetylamino acid is N-acetyl-D-amino acid, such as N-acetyl-D-leucine, N-acetyl-D-valine, N-acetyl-D-alanine, and N-acetyl-D-phenylalanine, preferably N-acetyl-D-leucine, and N-acetyl-D-valine, particularly preferably N-acetyl-D-leucine.

Examples of N-formylamino acid are N-formyl-L-amino acid, such as N-formyl-L-leucine, N-formyl-L-alanine, and N-formyl-L-phenylalanine, preferably N-formyl-L-leucine, and N-formyl-L-alanine, particularly preferably N-formyl-L-leucine.

The aldehyde compound is added to the reaction system as a racemizing reagent to enhance the racemization of N-benzyl-2-amino-3-methoxypropionamide.

Examples of the aldehyde compound is preferably a benzaldehyde compound, such as 3,5-dichlorosalicylaldehyde, 5-nitro-salicylaldehyde, 2-nitrobenzaldehyde, 4-nitrobenzaldehyde, and 2,4-dinitrobenzaldehyde, and pyridoxalphosphate, more preferably a nitrobenzaldehyde compound for letting the isomerization-crystallization proceed at a higher efficiency, particularly preferably 5-nitro-salicylaldehyde.

The usage amount of the aldehyde compound is, to Compound (2) of 1 mol, usually 0.01 mol to 0.5 mol, preferably 0.02 mol to 0.3 mol, particularly preferably 0.03 mol to 0.2 mol. The amount the aldehyde compound in this range allows the racemization to efficiently proceed.

The aldehyde compound may exist in the reaction system at the start of the reaction or may be provided in the course of the reaction. The aldehyde compound may be provided all at once or in separated multiple times.

In the reaction of Compound (2) with N-acetylamino acid or N-formylamino acid, the sequence of providing these compounds may be appropriately selected. Each of these compounds may be provided into the reaction system all at once (overall providing) or may be provided in separated multiple times (divisional providing).

Normally, N-acetylamino acid or N-formylamino acid is provided into the reaction system containing Compound (2) and the solvent. Consequently, (R) N-benzyl-2-amino-3-methoxypropionamide reacts with N-acetylamino acid or N-formylamino acid to generate and crystallize a salt. After the salt is crystallized, N-benzyl-2-amino-3-methoxypropionamide remaining in the reaction system is racemized and further, (R) N-benzyl-2-amino-3-methoxypropionamide reacts with N-acetylamino acid or N-formylamino acid to generate and crystallize a salt.

In overall providing, a salt is generated and crystallized all at once to lower the fluidity of the slurry, so that the reaction efficiency sometimes degrades. Under this circumstance, increasing the temperature in an attempt of raising the fluidity sometimes generates by-product to degrade the yield, the chemical purity, and the diastereomeric excess. Alternatively, increasing the amount of the solvent in an attempt of raising the fluidity may result in the higher cost to lower the productivity. With the foregoing problems in view, divisional providing is more preferably in the present invention. Divisional providing generates and crystallizes a desired salt little by little, inhibiting generation and crystallization of undesired salts, so that the isomerization-crystallization can be accomplished without degrading the reaction efficiency. Divisional providing makes it possible to obtain desired salt of (R) N-benzyl-2-amino-3-methoxypropionamide and N-acetylamino acid or N-formylamino acid at high yield, high chemical purity, high diastereomeric excess, and high productivity, which consequently can obtain target lacosamide at high yield, high chemical purity, high diastereomeric excess, and high productivity.

The resolving reagent in the solid form may be directly provided, the resolving reagent in the mixed form with the solvent may be provided, or the resolving reagent in the solid and mixture forms may be provided in combination. The solvent to be mixed with the resolving reagent can be the same as the solvent used in the isomerization-crystallization process.

For example, when the resolving reagent in the solid form is provided in separated multiple times, the number of times of providing is satisfactorily selected depending on the largeness of the reaction container, and is usually twice or more. The number of times of providing is preferably twice to 20 times, more preferably three times to ten times, furthermore preferably three times to five times.

For example, when the resolving reagent in the mixture form with the solvent, the number of times of providing is satisfactorily selected depending on the largeness of the reaction container, and may be provided by means of dropping. The number of times of providing is preferably twice or more, more preferably three times or more.

In the isomerization-crystallization process, the total usage amount of the resolving reagent is, to Compound (2) of 1 mol, usually 0.5 mol to 3 mol, preferably 0.6 mol to 2 mol, more preferably 0.8 mol to 1.5 mol, particularly preferably 0.9 mol to 1.3 mol. The usage amount of N-acetylamino acid when N-acetylamino acid is solely used as the resolving reagent, the usage amount of N-formylamino acid when N-formylamino acid is solely used as the resolving reagent, and the total usage amount of N-acetylamino acid and N-formylamino acid when N-acetylamino acid and N-formylamino acid are used as the resolving reagent in combination with each other are all within the above range. The usage within this range makes it possible to obtain a salt of (R) N-benzyl-2-amino-3-methoxypropionamide and N-acetylamino acid or N-formylamino acid which salt is high in diastereomeric excess, and further increase the yield of the salt of (R) N-benzyl-2-amino-3-methoxypropionamide and N-acetylamino acid or N-formylamino acid.

When the resolving reagent is provided into the reaction system containing Compound (2) and the solvent all at once or in separated multiple times, the total usage amount of N-acetylamino acid and N-formylamino acid is within the above range.

When the resolving reagent is provided into the reaction system containing Compound (2) and the solvent in separated multiple times, the usage amount in each application is, to Compound (2) of 1 mol, 0.1 mol to 1 mol, preferably 0.2 mol to 0.8 mol, more preferably 0.3 mol to 0.7 mol, particularly preferably 0.4 mol to 0.6 mol.

When the resolving reagent is provided into the reaction system containing Compound (2) and the solvent in separated multiple times, the upper limit of the usage amount for the first application to the total usage amount, which means the amount provided for the initial stage of the reaction, is preferably 0.8 times or less, more preferably 0.7 times of less, further preferably 0.6 times or less, particularly preferably 0.5 times or less. The lower limit is preferably 0.1 times or more, more preferably 0.2 times or more, further preferably 0.3 times or more, particular preferably 0.4 times or more.

This usage amount for the first application within this range makes it possible to obtain a salt of (R) N-benzyl-2-amino-3-methoxypropionamide and N-acetylamino acid or N-formylamino acid high in diastereomeric excess, and also enhance the yield of the salt of (R) N-benzyl-2-amino-3-methoxypropionamide and N-acetylamino acid or N-formylamino acid. Providing the resolving reagent in separated multiple times makes the reaction possible to efficiently proceed, so that the salt can be obtained at high productivity, which is economic and preferably from the industrial aspect.

The solvent is not particularly limited as far as the reaction proceeds. Examples of the solvent are an alcoholic solvent such as aliphatic alcohol exemplified by methanol, ethanol, isopropanol, and normal propanol; an ester-based solvent such as acetate ester exemplified by methyl acetate, ethyl acetate, propyl acetate, isopropyl acetate, butyl acetate, and isobutyl acetate; a hydrocarbon solvent exemplified by toluene, xylene, and acetonitrile; a ketone solvent exemplified by methyl ethyl ketone, methyl isobutyl ketone, and acetone. The above solvents can be mixed when being used.

Among these examples, aliphatic alcohol such as isopropanol, an ester-based solvent such as acetate ester, toluene, methyl isobutyl ketone are preferable, an ester-based solvent is more preferably for letting the isomerization-crystallization proceed at high efficiency. Above all, acetate ester is further preferably, and isopropyl acetate is particularly preferable.

If an ester-based solvent is used as the solvent, the ester solvent may be substantially solely used may be a mixed solvent with another solvent. However, a single solvent of an ester-based solvent is preferable from the aspects of costs and productivity efficient. Above all, a single solvent of acetic ester is preferable, and a single solvent of isopropyl acetate is more preferable. Here, a single solvent of an ester-based solvent means that the content of the component except of the ester-based solvent in the solvent is usually 5 wt % or less, preferably 1 wt % or less, more preferably 0.5 wt % or less, further preferably 0.1 wt % or less.

The usage amount of the solvent is, to Compound (2) of 1 gram, usually 50 mL or less, preferably 20 mL or less, more preferably 18 mL or less, further preferably 16 mL or less. Using the solvent of this upper limit or less is preferable from the aspects of cost and productivity. The lower limit of the usage amount of the solvent is not limited as far as the solvent functions as a solvent, and is, to Compound (2) of 1 gram, usually 2.5 mL or more, preferably 3.5 mL or more, more preferably 5 mL or more, further preferably 7.5 mL or more.

(Reaction Condition)

The temperature at the isomerization-crystallization is usually 65° C. or less, preferably 62° C. or less, more preferably 60° C. or less, more preferably 58° C. or less, particularly preferable 55° C. or less. The reaction temperature outside this range has a possibility that the generated salt may have low in the yield, the chemical purity, and the diastereomeric excess. Above all, the reaction temperature of the upper limit of this range or less can enhance the yield, suppressing generation of by-product. The lower limit is preferably 20° C. or more, more preferably 25° C. or more, more preferably 30° C. or more, particularly preferably 40° C. or more. The reaction temperature of the lower limit of this range or more makes the reaction possible to achieve at high productivity, so that the yield can be enhanced.

The pressure at the isomerization-crystallization is usually a normal pressure, and the reaction time can be appropriately selected. The reaction time is usually 0.5 hours to 100 hours.

In the isomerization-crystallization process, the crystallization is preferably carried out by controlling the concentrations and temperature of racemic N-benzyl-2-amino-3-methoxypropionamide and N-acetylamino acid or N-formylamino acid. For the above, the isomerization-crystallization process preferably uses a reactor having, for example, a stirring tank and a heating-and-cooling jacket.

In the isomerization-crystallization process, the order of charging racemic N-benzyl-2-amino-3-methoxypropionamide, an aldehyde compound, and the resolving reagent is not limited. For example, the reactor is charged with one or more components of racemic N-benzyl-2-amino-3-methoxypropionamide, an aldehyde compound, and the resolving reagent along with the solvent as a base solution and then is provided with the remaining component(s) in the form of a providing liquid under the reaction condition. Above all, it is preferable that the reactor is charged with racemic N-benzyl-2-amino-3-methoxypropionamide, an aldehyde compound and the solvent and is then provided with the resolving reagent, or the reactor is charged with racemic N-benzyl-2-amino-3-methoxypropionamide and the solvent and is then provided with an aldehyde compound and the resolving reagent.

(Crystal of Salt)

The isomerization-crystallization process of the present invention can obtain the crystal of a salt of (R) N-benzyl-2-amino-3-methoxypropionamide and N-acetylamino acid or N-formylamino acid which salt has a high chemical purity and a high diastereomeric excess at a high yield. The chemical purity is preferably 90% or more, more preferably 95% or more, more preferably 98% or more, particularly preferably 99% or more. The diastereomeric excess is preferably 90% de or more, more preferably 95% de or more, more preferably 98% de or more, particularly preferably 99% de or more. The high chemical purity and the high diastereomeric excess of the crystal of salt of (R)—N-benzyl-2-amino-3-methoxypropionamide and N-acetylamino acid or N-formylamino acid makes it possible to obtain lacosamide having a high chemical purity and a high diastereomeric excess through the acetylation process.

The isomerization-crystallization process of the present invention achieves a high yield of an R-configuration salt per the resolving reagent of 1 MR, which means that the salt obtained through the reaction contains a large amount of (R) N-benzyl-2-amino-3-methoxypropionamide. This further means that the isomerization-crystallization process has a high reaction efficiency. Here, the term "MR" of the resolving reagent represents a ratio of a usage amount (mol) of the resolving reagent to a usage amount (mol) of racemic N-benzyl-2-amino-3-methoxypropionamide.

The yield of an R-configuration salt per the resolving reagent of 1 MR can be calculated by the following equation.

$Y_R = Y \times (R_R/100)/A$ $R_R = (R_{RS} + 100)/2$ $R_{RS} = R_R - R_S$ $R_R + R_S = 100$ $Y_R$: yield (%) of an R-configuration salt per the resolving reagent of 1 MR
Y: yield (%) of a salt to racemic compound
A: molar ration (MF) of the resolving reagent to racemic compound
$R_R$: ratio (%) of R-configuration compound included in a salt
$R_S$: ratio (%) of S-configuration compound included in a salt
$R_{RS}$: diastereomeric excess (% de) of the salt obtained through the reaction Here, the symbol Y represents a percentage (%) of a molar ratio of an amount (mol) of the salt obtained through the reaction to a usage amount (mol) of the racemic compound, and the symbol A represents a molar ratio (MR) of a usage amount (mol) of the resolving reagent to a usage amount (mol) of the racemic compound.

The crystal of the salt of (R) N-benzyl-2-amino-3-methoxypropionamide and the resolving reagent is a compound (hereinafter sometimes referred to as "Compound (5)") expressed following Formula (5) (in the formula, the symbol "$Z^-$" represents a free anion of the resolving reagent). Compound (5) is efficacious for an intermediate to produce lacosamide.

[Formula 4]

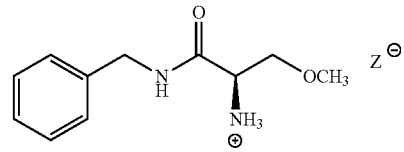

(5)

A typical crystal of Compound (5) has a powder X-ray diffraction pattern that exhibits peaks at the diffraction angles 2θ of near to 17° to 19° and near to 24.5° to 26.5°.

When N-acetylamino acid is used as the resolving reagent in Compound (5), the obtained salt is a compound represented by the following Formula (6) (in the formula, the symbol "$Z_1^-$" represents a free anion of N-acetylamino acid). Compound (6) is efficacious for an intermediate to produce lacosamide.

[Formula 5]

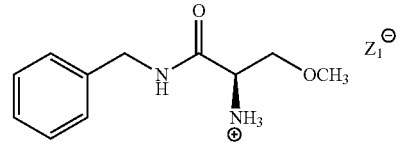

(6)

A typical crystal of Compound (6) has a powder X-ray diffraction pattern that exhibits peaks at the diffraction angles 2θ of near to 17.5° to 19° and near to 24.5° to 26°, preferably at the diffraction angles 2θ of near to 6° to 7.5°, near to 14.5° to 16°, near to 17.5° to 19°, and near to 24.5° to 26°.

The crystal of Compound (6) is highly filterable and is easily handled, and is therefore preferably applied to producing in the industrial scale.

When N-acetyl-D-leucine is used as N-acetylamino acid in Compound (6), the salt thereof is compounds (hereinafter, sometimes referred to as Compound (3)) represented by the following Formula (3).

[Formula 6]

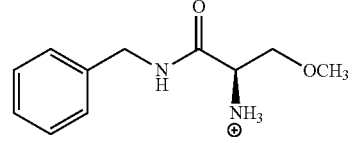

(3)

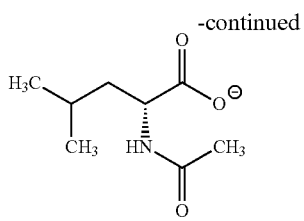

A typical crystal of Compound (3) has a powder X-ray diffraction pattern as shown in FIG. 1. Specifically, the crystal of Compound (3) has a powder X-ray diffraction pattern that exhibits peaks at the diffraction angles 2θ of near to 18° to 19° and near to 25° to 26°, preferably at the diffraction angles 2θ of near to 6° to 7°, near to 15° to 16°, near to 18° to 19°, and near to 25° to 26°, more preferably at the diffraction angles 2θ of near to 6° to 7°, near to 12.5° to 13.5°, near to 15° to 16°, near to 18° to 19°, near to 23° to 24°, and near to 25° to 26°. Among these peaks, the peak at the diffraction angles 2θ of near to 6° to 7° is the highest. The crystal of Compound (3) preferably has a characteristic profile characterized by the most intensive peak at the diffraction angles 2θ of near to 6° to 7°.

Compound (3) is efficacious as an intermediate to produce lacosamide. Furthermore, the crystal of Compound (3) is highly filterable and is easily handled, and is therefore preferably used to producing in the industrial scale.

Specifically, the crystal of Compound (3) has a powder X-ray diffraction pattern as shown in, for example, Table 1 of Example 1 to be detailed follow. Specifically, the crystal of Compound (3) has a powder X-ray diffraction pattern that exhibits peaks at the diffraction angles 2θ of near to 6.3°, near to 15.8°, near to 18.1 to 18.3°, near to 23.2° to 23.4°, and near to 25.2°, preferably at the diffraction angles 2θ of near to 6.3°, near to 6.6°, near to 12.9°, near to 15.8°, near to 18.1 to 18.3°, near to 23.2° to 23.4°, and near to 25.2°. Among these peaks, the peak at the diffraction angle 2θ of near to 6.3° is the highest.

When N-acetyl-D-valine is used as N-acetylamino acid in Compound (6), the salt thereof is compounds (hereinafter, sometimes referred to as Compound (7)) represented by the following Formula (7).

[Formula 7]

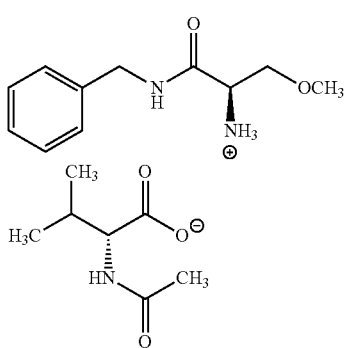

(7)

Figure 3:
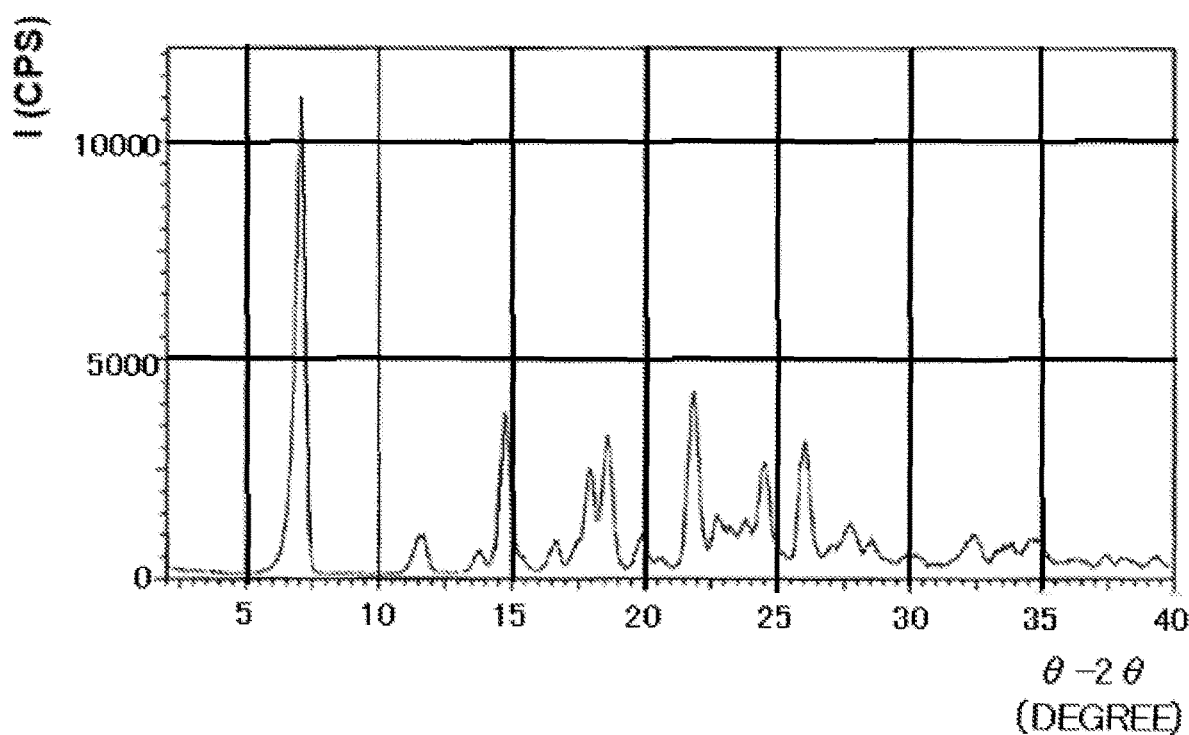
FIG. 3 is a graph plotting a powder X-ray diffraction pattern of the crystal of a salt of (R) N-benzyl-2-amino-3-methoxypropionamide and N-acetyl-D-valine obtained in Example 7.

The typical crystal of Compound (7) has a powder X-ray diffraction pattern as shown in FIG. 3. Specifically, the crystal of Compound (7) has a powder X-ray diffraction pattern that exhibits peaks at the diffraction angles 2θ of near to 18° to 19° and near to 24.5° to 25.5°, preferably at the diffraction angles 2θ of near to 6.5° to 7.5°, near to 14.5° to 15.5°, near to 18° to 19°, near to 24.5° to 25.5°, more preferably at the diffraction angles 2θ of near to 6.5° to 7.5°, near to 14.5° to 15.5°, near to 18° to 19°, near to 21.5° to 22.5°, near to 24.5° to 25.5°. Among these peaks, the peak at the diffraction angles 2θ of near to 6.5° to 7.5° is the highest.

The crystal of Compound (7) is efficacious as an intermediate to produce lacosamide. Furthermore, the crystal of Compound (7) is highly filterable and is easily handled, and is therefore preferably applied to producing sis in the industrial scale.

Specifically, the crystal of Compound (7) has a powder X-ray diffraction pattern as shown in, for example, Table 5 of Example 7 to be detailed follow. Specifically, the crystal of Compound (7) has a powder X-ray diffraction pattern that exhibits peaks at the diffraction angles 2θ of near to 7°, near to 14.8°, near to 18.7°, near to 21.9°, and near to 24.6°. Among these peaks, the peak at the diffraction angle 2θ of near to 7° is the highest.

When N-formylamino acid is used as the resolving reagent in Compound (5), Compound (5) is a compound represented by the following Formula (8) (in the formula, the symbol "$Z_2^-$" represents a free anion of N-formylamino acid).

[Formula 8]

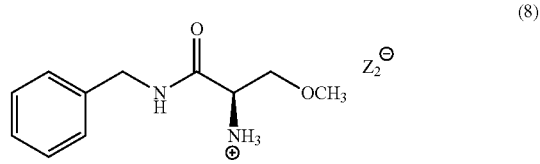

(8)

A typical crystal of a Compound (8) has a powder X-ray diffraction pattern that exhibits peaks at the diffraction angles 2θ of near to 17.5° to 19°, and near to 24.5° to 26°, preferably at the diffraction angles 2θ of near to 9° to 10.5°, near to 11.5° to 13°, near to 17.5° to 19°, and near to 24.5° to 26°.

The crystal of Compound (8) is efficacious as an intermediate to produce lacosamide. Furthermore, the crystal of Compound (8) is highly filterable and is easily handled, and is therefore preferably applied to producing in the industrial scale.

When N-formyl-L-leucine is used as N-formylamino acid in Compound (8), Compound (8) is compound represented by the following Formula (9) (hereinafter, sometimes referred to as "Compound (9)").

[Formula 9]

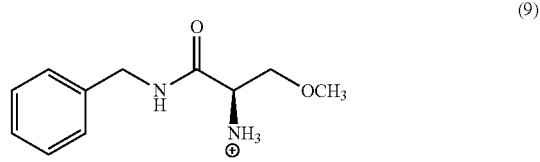

(9)

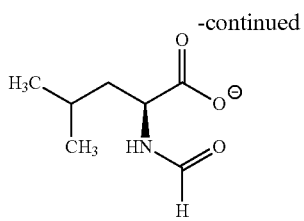

Figure 2:
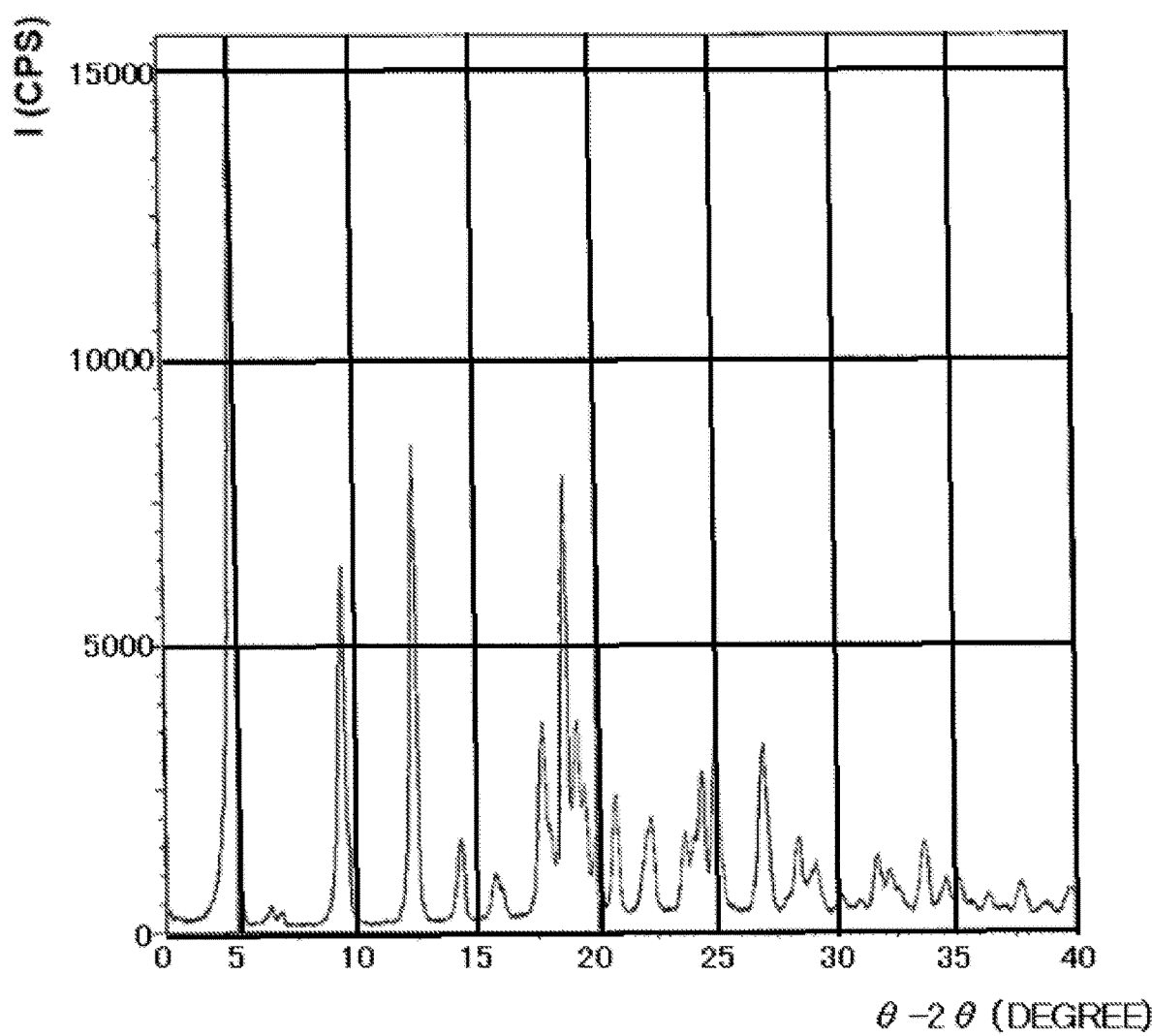
FIG. 2 is a graph plotting a powder X-ray diffraction pattern of the crystal of a salt of (R) N-benzyl-2-amino-3-methoxypropionamide and N-formyl-L-leucine obtained in Example 6.

The typical crystal of Compound (9) has a powder X-ray diffraction pattern as shown in FIG. 2. Specifically, the crystal of Compound (9) has a powder X-ray diffraction pattern that exhibits peaks at the diffraction angles 2θ of near to 18° to 19° and near to 24.5° to 25.5°, preferably at the diffraction angles 2θ of near to 9° to 10°, near to 12° to 13°, near to 18° to 19°, and near to 24.5° to 26°, more preferably at the diffraction angles 2θ of near to 4.5° to 5.5°, near to 9° to 10°, near to 12° to 13°, near to 18° to 19°, near to 24.5° to 25.5°, and near to 26.5° to 27.5°. Among these peaks, the peak at the diffraction angles 2θ of near to 4.5° to 5.5° is the highest.

The crystal of Compound (9) is efficacious as an intermediate to produce lacosamide. Furthermore, the crystal of Compound (9) is highly filterable and is easily handled, and is therefore preferably applied to produce in the industrial scale.

Specifically, the crystal of Compound (9) has a powder X-ray diffraction pattern as shown in, for example, Table 3 of Example 6 to be detailed follow. Specifically, the crystal of Compound (9) has a powder X-ray diffraction pattern that exhibits peaks at the diffraction angles 2θ of near to 4.9°, near to 9.4°, near to 12.4°, near to 18.7°, near to 24.9°, and near to 26.9°. Among these peaks, the peak at the diffraction angle 2θ of near to 4.9° is the highest.

When N-formyl-L-alanine is used as N-formylamino acid in Compound (8), Compound (8) is compounds represented by the following Formula (10) (in the formula, sometimes referred to as "Compound (10)").

[Formula 10]

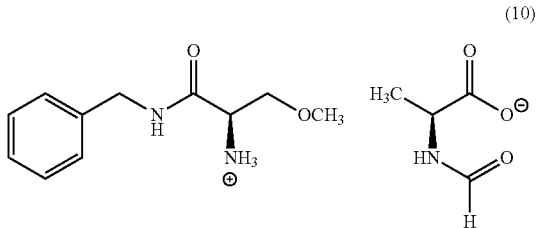

(10)

Figure 4:
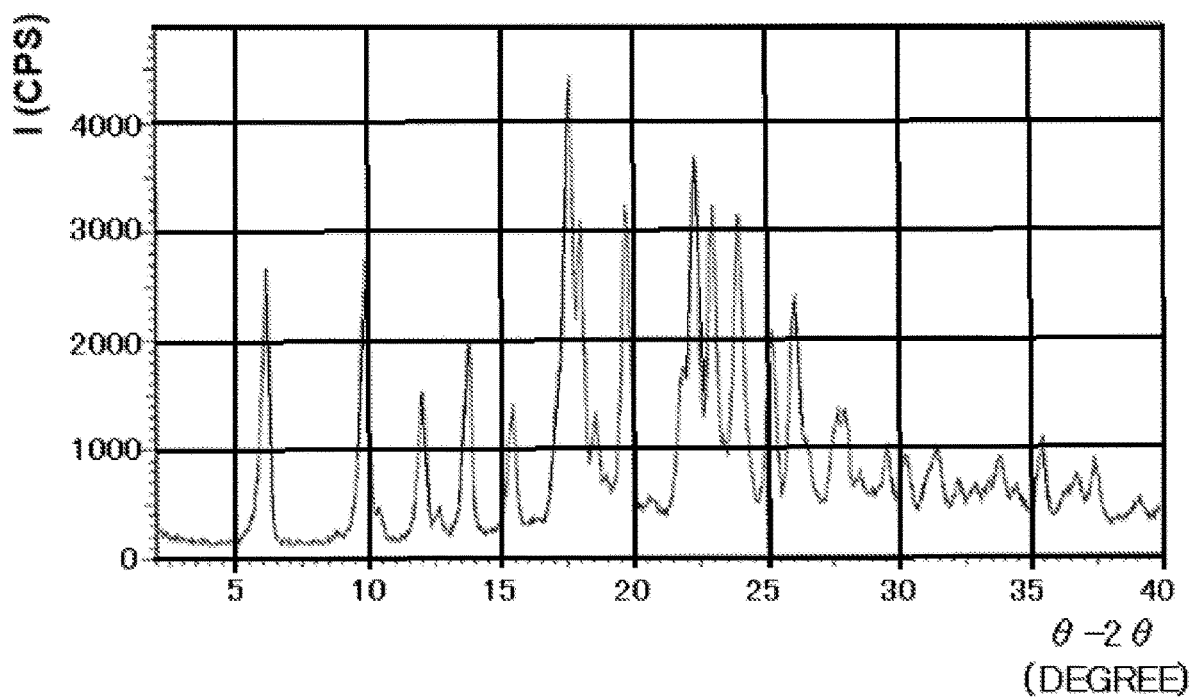
FIG. 4 is a graph plotting a powder X-ray diffraction pattern of the crystal of a salt of (R) N-benzyl-2-amino-3-methoxypropionamide and N-formyl-L-alanine obtained in Example 8.

The typical crystal of Compound (10) has a powder X-ray diffraction pattern as shown in FIG. 4. Specifically, the crystal of Compound (10) has a powder X-ray diffraction pattern that exhibits peaks at the diffraction angles 2θ of near to 17.5° to 18.5°, near to 25° to 26°, preferably at the diffraction angles 2θ of near to 9.5° to 10.5°, near to 11.5° to 12.5°, near to 17.5° to 18.5°, and near to 25° to 26°, more preferably at the diffraction angles 2θ of near to 9.5° to 10.5°, near to 11.5° to 12.5°, near to 17.5° to 18.5°, near to 19.5° to 20.5°, near to 22° to 23°, and near to 25° to 26° Among these peaks, the peak at the diffraction angles 2θ of near to 17.5° to 18.5° is the highest.

The crystal of Compound (10) is efficacious as an intermediate to produce lacosamide. Furthermore, the crystal of Compound (10) is highly filterable and is easily handled, and is therefore preferably used to producing in the industrial scale.

Specifically, the crystal of Compound (10) has a powder X-ray diffraction pattern as shown in, for example, Table 6 of Example 8 to be detailed follow. Specifically, the crystal of Compound (10) has a powder X-ray diffraction pattern that exhibits peaks at the diffraction angles 2θ of near to 9.9°, near to 12.0°, near to 17.8°, near to 19.8°, near to 22.4°, near to 24.0°, and near to 25.3°. Among these peaks, the peak at the diffraction angle 2θ of near to 17.8° is the highest.

In the present invention, a powder X-ray diffraction pattern can be measured by X-ray diffraction measurement using CuKα ray in accordance with any method known to public. Since a diffraction angle (2θ) in powder X-ray diffraction generally would have an error within a usual range of ±0.2° due to an error caused in preparing the sample (e.g., the sample height) and a device error (e.g., plane sample error), it should be understand that the values of ±0.2° from the above values of the diffraction angle are also included in the range.

Accordingly, a crystal having a diffraction angle at a peak coinciding with the above range, allowing an error of about ±0.2°, is also included in the present invention as well as a crystal having a diffraction angle at a peak completely coinciding with the above range. In the above description, "near" means a value of diffraction angle (2θ+0.2°).

<Amination Process>

Compound (2) can be synthesized by the method described in Patent Literature WO2010/052011 or a combination of schemes of organic synthesizing publicly known, or can be one commercially available.

For example, the compound represented by Formula (2) can be synthesized by aminating a compound (hereinafter, sometimes referred to as "Compound (4)") expressed by the following Formula (4) (in the formula, the symbol "X" represents a leaving group). The amination can be accomplished by causing Compound (4) to react with an aminating reagent. An aminating reagent is preferably an ammonia compound.

[Formula 11]

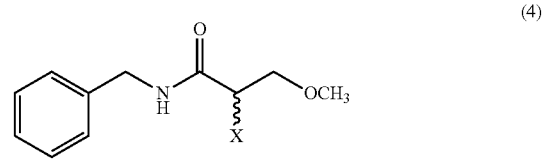

(4)

Examples of the free radical represented by the symbol "X" are a halogen atom (e.g., a chlorine atom, a bromine atom, an iodine atom), a methanesulfonyloxy group, a p-toluenesulfonyloxy group, an acetoxy group, a diphenylphosphoryloxy group, preferably a halogen atom, preferably a bromine atom from the industrial aspects.

Examples of the ammonia compound are ammonia and ammonium hydroxide, particularly preferable ammonium hydroxide.

The usage amount of the ammonia compound is, to Compound (4) of 1 mol, usually 10 mol to 30 mol, preferably 15 mol to 25 mol.

The reaction can be carried out using a solvent. The solvent is not particularly limited as far as the reaction proceeds. Examples of the solvent are an alcoholic solvent such as methanol, ethanol, isopropanol; an hydrocarbon solvent such as toluene, xylene, acetonitrile; and a halogen solvent such as dichloromethane, chloroform. Examples of the solvent is preferably an alcoholic solvent, particularly preferably methanol or ethanol. These solvents may be used solely or in combination of two or more.

The usage amount of the solvent is, to Compound (4) of 1 mol, usually 200 mL to 1000 mL, preferably 300 mL to 800 mL.

The reaction temperature is usually 70° C. to 100° C., preferably 75° C. to 95° C.

The reaction time is usually 2 hours to 8 hours, preferably 3 hours to 6 hours.

The pressure at the reaction is usually 0.1 MPa to 0.9 Mpa, preferably 0.2 MPa to 0.6 MPa.

Compound (4) can be produced by the method described in Patent Literature WO2010/052011 or a combination of schemes of organic synthesizing publicly known, or can be one commercially available.

For example, Compound (4) can be synthesized by using 2,3-dibromomethylpropionate or 2,3-dibromoethylpropionate commercially available as a substrate and causing the substrate to react with sodium methoxide and benzylamine in the solvent.

The usage amount of sodium methoxide is, to the substrate of 1 mol, usually 1 mol to 10 mol, preferably 1 mol to 5 mol.

The usage amount of benzylamine is, to the substrate of 1 mol, usually 1 mol to 100 mol, preferably 1 mol to 50 mol, particularly preferably 1 mol to 10 mol.

The solvent is not particularly limited as far as the reaction proceeds, but may be methanol, tetrahydrofuran (hereinafter, may sometimes referred to as "THF"), or toluene. These solvents may be used solely or in combination of two or more. The solvent is preferably methanol or THF, particularly preferably methanol.

The usage amount of the solvent is, to the substrate of 1 mol, usually 0.1 L to 30 L, preferably 0.5 L to 10 L, particularly preferably 0.7 L to 5 L.

The reaction temperature is usually −20° C. to 80° C., preferably −10° C. to 70° C.

The reaction time is usually 0.1 hours to 100 hours, preferably 0.5 hours to 90 hours. The pressure at the reaction is usually normal pressure.

<Acetylation Process>

Lacosamide can be obtained through carrying out an acetylation process on the salt obtained in the isomerization-crystallization process. Specifically, lacosamide is obtained by acetylating (R) N-benzyl-2-amino-3-methoxypropionamide contained in the salt obtained in the isomerization-crystallization process.

The salt obtained in the isomerization-crystallization process may be directly applied to the acetylation process or may be isolated from the reaction system in an ordinary procedure and then applied to the acetylation process. For example, the salt obtained in the isomerization-crystallization process may be refined through recrystallization, distillation, or chromatography, and then applied to the acetylation process.

The acetylation process of the present invention is preferably (i) a process of acetylating a salt of (R) N-benzyl-2-amino-3-methoxypropionamide and N-acetylamino acid or N-formylamino acid, or (ii) a process of acetylating (R) N-benzyl-2-amino-3-methoxypropionamide.

(i) Process of acetylating the salt of (R) N-benzyl-2-amino-3-methoxypropionamide and N-acetylamino acid or N-formylamino acid:

This process obtains lacosamide by causing the salt obtained in the isomerization-crystallization process to react with an acetylating reagent in the solvent.

Examples of the acetylating reagent are halogenated acetyl such as acetyl chloride or acetyl bromide, acetic acid, acetic anhydride, and N-acetylimidazole, preferably halogenated acetyl, acetic acid, or acetic anhydride from the viewpoint of reactivity, more preferably acetyl chloride or acetic anhydride, particularly preferably acetic anhydride.

The usage amount of the acetylating reagent is, to 1 mol of the salt of (R) N-benzyl-2-amino-3-methoxypropionamide and N-acetylamino acid or N-formylamino acid of 1 mol, usually 0.5 mol to 20 mol, preferably 0.8 mol to 10 mol, particularly preferably 1 mol to 5 mol.

In order to enhance the reactivity, it is preferable to add a base into the reaction system. Examples of the base are inorganic base compounds such as sodium hydrogencarbonate, sodium acetate, potassium carbonate, potassium hydrogencarbonate, and organic base compounds such as triethylamine, pyridine, p-(N,N-dimethylamino)pyridine, preferably sodium hydrogencarbonate, sodium acetate, and potassium carbonate.

The usage amount of the base is, to the salt of (R) N-benzyl-2-amino-3-methoxypropionamide and N-acetylamino acid or N-formylamino acid of 1 mol, usually 0.5 mol to 20 mol, preferably 0.8 mol to 10 mol, particularly preferably 1 mol to 5 mol.

The solvent is not particularly limited as far as the reaction proceeds. Examples of the solvent is an alcoholic solvent such as methanol, ethanol, isopropyl alcohol, an ether solvent such as THF, dioxane, and methyl-t-butyl ether (MTBE), a carbohydrate solvent such as toluene, xylene, methylene chloride, an ester-based solvent such as methyl acetate, ethyl acetate, isopropyl acetate, butyl acetate, and water. These solvents may be used solely or in combination of two or more. The solvent is preferably a mixed solvent of ethyl acetate and water, simple water, and an aqueous solution containing water at the concentration of 95 vol % or more.

When a mixed solvent of ethyl acetate and water is used as the solvent, the content of water is, to the ethyl acetate, usually 80 vol % or less, preferably 60 vol % or less.

When the solvent is a simple water solvent or an aqueous solution containing water at the concentration of 95 vol % or more, lacosamide, which is the target material, precipitates in the reaction system and therefore easily isolated and recollect through, for example, filtration. In this example, the presence of an inorganic salt such as sodium chloride, potassium hydrogencarbonate, or potassium carbonate in the reaction system can enhance the efficiency in precipitation of lacosamide.

The filtrate from which lacosamide has been isolated and recollected contains N-acetylamino acid or N-formylamino acid. Addition of acid such as formic acid, hydrochloric acid, and sulfuric acid to make the filtrate acid can precipitate crystalline form of N-acetylamino acid and N-formylamino acid. This can recollect N-acetylamino acid or N-formylamino acid and reduce the cost, and therefore, is preferable for an industrial producing method.

The usage amount of the solvent is, to the salt of (R) N-benzyl-2-amino-3-methoxypropionamide and N-acetylamino acid or N-formylamino acid of 1 mol, usually 1 mL to 100 mL, preferably 2 mL to 50 mL, particularly preferably 3 mL to 30 mL.

The reaction temperature is usually 10° C. to 40° C., preferably 15° C. to 30° C.

The reaction time is usually 0.1 hours to 5 hours, preferably 0.5 hours to 3 hours.

The pressure at the reaction is usually normal pressure.

In this process, the salt obtained in the isomerization-crystallization process is preferably caused to react with the acetylating reagent in the presence of the base in the simple water solvent or an aqueous solution.

(ii) Process of Acetylating (R) N-benzyl-2-amino-3-methoxypropionamide:

(R) N-benzyl-2-amino-3-methoxypropionamide is isolated from N-acetylamino acid or N-formylamino acid by causing the salt obtained in the isomerization-crystallization process to react with acid in the solvent, and the obtained (R) N-benzyl-2-amino-3-methoxypropionamide is further caused to react with an acetylating reagent to obtain lacosamide.

Examples of the acid are an inorganic acid such as nitric acid, sulfuric acid, hydrochloric acid, phosphorus acid, a carboxylic acid such as formic acid, acetic acid, oxalic acid, succinic acid, malonic acid, fumaric acid, an alkane sulfonic acid such as methanesulfonic acid. Above all, hydrochloric acid, sulfuric acid, formic acid, and acetic acid is preferable, and hydrochloric acid or sulfuric acid is more preferable from an economical aspect.

The solvent and the acetylating reagent can be ones described in the above process (i).

In order to enhance the reactivity of the acetylation, it is preferable to add a base into the reaction system. The base can be one listed in the above process (i).

N-acetylamino acid or N-formylamino acid precipitates in the reaction system by causing the salt obtained in the isomerization-crystallization process to react with acid in the solvent. The precipitated N-acetylamino acid or N-formylamino acid can be easily isolated from the reaction system in an ordinary procedure exemplified by filtration. The isolated N-acetylamino acid or N-formylamino acid can be recollected in the form of the crystal with ease by drying, and therefore this process is preferable from the industrial viewpoint.

The usage amount of the acid is, to the salt of (R) N-benzyl-2-amino-3-methoxypropionamide and N-acetylamino acid or N-formylamino acid of 1 mol, usually 0.5 mol to 10 mol, preferably 0.7 mol to 5 mol, particularly preferably 0.8 mol to 3 mol.

The reaction temperature with the acid is usually 5° C. to 40° C., preferably 10° C. to 30° C.

The reaction time with the acid is usually 3 hours or less, preferably 2 hours or less.

The pressure at the reaction with the acid is usually normal pressure.

Lacosamide can be obtained through the acetylation (R) N-benzyl-2-amino-3-methoxypropionamide by providing the acetylating reagent, the base, and the additional solvent as required into the reaction system in which N-acetylamino acid or N-formylamino acid has precipitated or the reaction system from which N-acetylamino acid or N-formylamino acid has been isolated and removed. The reaction conditions (the usage amount of the acetylating reagent, the reaction temperature, the reaction time, and the reaction pressure) can be the same as those of the above process (i).

Lacosamide obtained in the above process (i) or (ii) may be refined in a publicly known scheme such as recrystallization or chromatography.

<Pharmaceutical Composition>

The present invention also relates to pharmaceutical compositions obtained by mixing lacosamide produced in the method of the present invention and a carrier pharmacologically allowable. Lacosamide obtained in the method of the present invention is prepared into ordinary dosage form (hereinafter referred to as "pharmaceutical drug products of the present invention") such as tablets, capsules, pills, glanules, capsules, troches, syrups, liquids and solutions, injections, and is administrated via a mouth or not via a mouth. In this case, the pharmaceutical drug products of the present invention can be prepared in an ordinary procedure using an effective amount of lacosamide obtained in the method for producing of the present invention and a carrier pharmaceutically allowable.

Examples of the "carrier pharmaceutically allowable" are various organic or inorganic carriers commonly used as pharmaceutical drug material such as a vehicle, a lubricant, a binder, and a disintegrator for solid drag products, and a solvent, a solubilization agent, a suspending agent, a tonicity agent, a buffer, and a soothing agent for liquid drag products.

Furthermore, additives such as a usual preservative, an antioxidant, a colorant, a sweetener, an adsorbent, and a wetting agent can be appropriately used in an appropriate amount.

Examples of the vehicle are lactose, saccharose, D-mannitol, D-sorbitol, starch, α-starch, cornstarch, dextrine, crystalline cellulose, low-substituted hydroxypropyl cellulose, carboxymethyl cellulose sodium salt, gum arabic, pullulan, light anhydrous silicic, synthetic aluminum silicate, and magnesium aluminometasilicate.

Examples of the lubricant are magnesium stearate, calcium stearate, talc, and colloidal silica.

Examples of the binder are α-starch, crystalline cellulose, saccharose, gum arabic, D-mannitol, trehalose, dextrine, pullulan, hydroxypropyl cellulose, hydroxypropylmethyl cellulose, polyvinylpyrrolidone, starch, sucrose, gelatin, methyl cellulose, carboxymethylcellulose, and carboxymethylcellulose sodium salt.

Examples of the disintegrator are lactose, sucrose, starch, carboxymethylcellulose, carboxymethylcellulose calcium, croscarmellose sodium, carboxymethylstarch sodium, light anhydrous silicic, and low-substituted hydroxypropyl cellulose.

Examples of the solvent are water for injection, saline, ringer solution, alcohol, propylene glycol, polyethylene glycol, macrogol, sesame oil, corn oil, olive oil, and cottonseed oil.

Examples of the solubilization agent are polyethylene glycol, propylene glycol, D-mannitol, trehalose, benzyl benzoate, ethanol, tris-aminomethane, cholesterol, triethanolamine, sodium carbonate, sodium citrate, sodium salicylate, and sodium acetate.

Examples of the suspending agent are surfactants such as stearyltriethanolamine, sodium lauryl sulfate, laurylaminopropionate, lecithin, benzalkonium chloride, benzethonium chloride, glyceryl monostearate; and hydrophilic polymers such as polyvinyl alcohol, polyvinylpyrrolidone, carboxymethyl cellulose sodium salt, methyl cellulose, hydroxymethyl cellulose, hydroxyethyl cellulose, hydroxypropyl cellulose, polysorbate, and polyoxyethylene hydrogenated castor oil.

Examples of a tonicity agent are glucose, D-sorbitol, sodium chloride, glycerin, and D-mannitol.

Examples of the buffer are a buffering solution such as phosphate, acetate, carbonate, and citrate.

An example of a soothing agent is benzyl alcohol.

Examples of the preservative are para-hydroxybenzonate esters, chlorobutanol, benzyl alcohol, phenethyl alcohol, dehydoacetic acid, and sorbic acid.

Examples of the antioxidant are sulfite, ascorbic acid, and α-tocophenol.

Examples of the colorant are water-soluble edible tar pigment (e.g., edible red No. 2 and No. 3, edible yellow No. 4 and No. 5, edible blue No. 1 and No. 2), insoluble lake pigments (e.g., aluminum salts of the above water-soluble edible tar pigments), natural pigments (e.g., β-carotene, chlorophyll, and red iron oxide).

Examples of the sweetener are sodium saccharin, glycyrrhizinate dipotassium, aspartame, and stevia.

The content of lacosamide in a pharmaceutical drug product of the present invention is different with, for example, dosage form and/or dose, and is, to the total weight of the entire pharmaceutical drug product, about 1 wt % to 100 wt %, more preferably about 8 wt % to 40 wt %.

The dose of the pharmaceutical drug product of the present invention is different with, for example, an object, an administration route, a target disease, and symptoms. When applied to an epileptic via mouth, the dose of lacosamide is usually about 0.1 mg/kg body weight to about 10 mg/kg body weight, preferably about 0.5 mg/kg body weight to about 10 mg/kg body weight, further preferably about 1 mg/kg body weight to about 4 mg/kg body weight. The pharmaceutical drug product of this does is preferably applied once to several times (e.g., once to three times) each day, depending on the individual symptoms.

EXAMPLES

Hereinafter, the present invention will now be further detailed with reference to Examples and Comparative Examples. However, it should be noted that the present invention is not limited to the following Examples.

In the description of Examples and Comparative Examples, the symbol "%" for a concentration and a content represents a "weight percent" unless otherwise specified. The ratio of a mixture solvent represents a "volume ratio" unless otherwise specified.

The correlation of the abbreviations in the following Examples and Comparative Examples are:
AMBA-ADL: salt of (R) N-benzyl-2-amino-3-methoxypropionamide and N-acetyl-D-leucine
AMBA: racemic N-benzyl-2-amino-3-methoxypropionamide
ADL: N-acetyl-D-leucine
AcOiPr: isopropyl acetate
5-NSA: 5-nitrosalicylaldehyde
SA: salicylaldehyde
IPA: isopropanol
AMBA-FLL: salt of (R) N-benzyl-2-amino-3-methoxypropionamide and N-formyl-L-leucine
FLL: N-formyl-L-leucine
AMBA-ADV: salt of (R) N-benzyl-2-amino-3-methoxypropionamide and N-acetyl-D-valine
ADV: N-acetyl-D-valine
FLA: N-formyl-L-alanine
AMBA-FLA: salt of (R) N-benzyl-2-amino-3-methoxypropionamide and N-formyl-L-alanine The following Examples and Comparative Example used AMBA synthesized according to the method described in Example (Example 1d) of WO2010/052011 (Japanese National Publication of International Patent Application No. 2012-508162).

Example 1 (Production of AMBA-ADL)

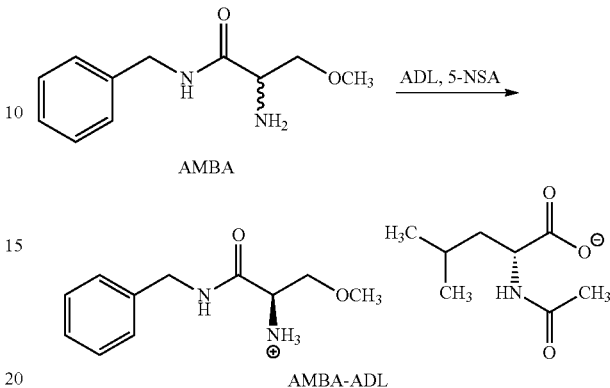

[Formula 12]

The material AMBA (8.33 g, 40.0 mmol) was mixed with the resolving reagent ADL (6.23 g, 36.0 mmol) in the solvent AcOiPr (83.0 mL) in the presence of the aldehyde compound 5-NSA (668 mg, 4.00 mmol), and then the mixture was stirred for 49 hours while the temperature of the mixture was controlled in the range of 50° C. to 55° C. The reacting liquid was cooled to 5° C. and then the precipitated crystal was recollected. The recollected crystal was washed with cool AcOiPr (25.0 mL) of the temperature of about 5° C., and the AMBA-ADL crystal was obtained (12.4 g, yield of 81%, yield of R-configuration salt per resolving reagent of 1 MR of 89.9%, chemical purity of 98.2 area %, diastereomeric excess=98.9% de). In Examples and Comparative Examples, a "yield" represents a percentage (%) of a molar ratio of an amount (mol) of a salt obtained through the reaction to a usage amount (mol) of the material AMBA.

$^1$H-NMR (400 MHz, DMSO-d6): δ 8.56-8.53 (m, 1H), 7.98 (d, J=8.0 Hz, 1H), 7.34-7.23 (m, 5H), 4.30-4.26 (m, 2H), 4.19-4.04 (m, 1H), 3.55-3.52 (m, 1H), 3.49-3.47 (m, 2H), 3.26 (s, 3H), 1.83 (s, 3H), 1.67-1.56 (m, 1H), 1.49-1.45 (m, 2H), 0.86 (dd, J=6.6 Hz, 10.0 Hz, 6H)

melting point: 135° C.

The powder X-ray diffraction pattern of the obtained crystalline AMBA-ADL was measured with an X-ray Diffractometers XRD-6000 (product of Shimadzu Corporation) under the following conditions.
X-ray source: CuKα
tube voltage: 40.0 kV
tube electric current: 40.0 mA
divergence: 1.00 deg
scattering: 1.00 deg
receiving: 0.15 mm
mode: continuous scanning
driving axis: 2θ/θ
data range: 2θ=5 to 40 deg
step: 0.02 deg
scanning velocity: 2 deg/min The obtained powder X-ray diffraction patterns are shown in Table 1 and FIG. 1.

TABLE 1

| 2θ (°) | RELATIVE INTENSITY |
|---|---|
| 6.0 | 12 |
| 6.3 | 100 |
| 6.6 | 29 |

TABLE 1-continued

| 2θ (°) | RELATIVE INTENSITY |
|---|---|
| 12.9 | 10 |
| 15.8 | 16 |
| 16.1 | 9 |
| 17.9 | 12 |
| 18.1 | 17 |
| 18.3 | 17 |
| 21.2 | 11 |
| 22.1 | 7 |
| 23.0 | 8 |
| 23.2 | 20 |
| 23.4 | 29 |
| 25.2 | 17 |
| 26.1 | 12 |
| 28.7 | 9 |
| 29.5 | 13 |

Example 2 (Production of AMBA-ADL)

The material AMBA (1.00 g, 4.80 mmol) was mixed with the resolving reagent ADL (0.42 g, 2.40 mmol) in the solvent AcOiPr (10.0 mL) in the presence of an aldehyde compound 5-NSA (80 mg, 0.48 mmol), and then the mixture was stirred for 24 hours while the temperature of the mixture was controlled in the range of 40° C. to 60° C. The reacting liquid was cooled to 5° C. and then the precipitated crystal was recollected. The recollected crystal was washed with cool AcOiPr (3.00 mL) of the temperature of about 5° C., and the AMBA-ADL crystal was obtained (0.86 g, yield of 47%, yield of R-configuration salt per resolving reagent of 1 MR of 92.8%, chemical purity of 99.7 area %, diastereomeric excess=99.4% de). Controlling the usage amount of the resolving reagent improves the yield of R-configuration salt per resolving reagent of 1 MR, so that the isomerization-crystallization can be efficiently accomplished.

The material AMBA (0.50 g, 2.40 mmol) was mixed with the resolving reagent FLL (0.38 g, 2.40 mmol) overall provided in place of ADL in a mixed solvent of AcOiPr (10.0 mL) and IPA (0.5 mL) in the presence of an aldehyde compound 5-NSA (20 mg, 0.12 mmol), and then the mixture was stirred for 16 hours at the temperature of 65° C. After the stirring, the reacting liquid is cooled to a room temperature and then the precipitated solid was recollected. The recollected sold was washed with a cool AcOiPr/IPA=9/1 solution (2.00 mL) of the temperature of about 5° C. and AMBA-FLL powder was obtained (0.68 g, yield of 77%, yield of R-configuration salt per resolving reagent of 1 MR of 73.4%, chemical purity of 99.6 area %, diastereomeric excess=89.7% de), which has a lower yield and a lower diastereomeric excess than the crystal obtained the above Example 1. In Examples and Comparative Examples, the "room temperature" means "25° C." unless otherwise specified.

In Examples and Comparative Examples, the chemical purities (area %) of AMBA-ADL, AMBA-FLL, AMBA-ADV, and AMBA-FLA were measured by means of HPLC under the following conditions.
  column: CAPCELL PAK C18 MGIII (100 mm×3.0 mm, 3 μm)
  mobile phase A: 10 mmol/L ammonium acetate aqueous solution
  mobile phase B: acetonitrile/water=9/1 (volume ratio)
  gradient B solution concentration: (10/0 min.)→(90/15 min.)→(90/20 min.)
  flow rate: 0.50 mL/min.
  injection volume: 3 μL
  detecting wavelength: 215 nm
  column temperature: 40° C.

The diastereomeric excesses (de %) of AMBA-ADL, AMBA-FLL, AMBA-ADV, and AMBA-FLA were measured by means of HPLC under the following conditions.
  column: Chiralcel OJ-H (250 mm×4.6 mm, 5 μm)
  mobile phase A: n-hexane solution containing diethylamine of 0.1% (volume %)
  mobile phase B: ethanol
  isocratic condition for mobile phase A/B=95/5 (volume ratio)
  flow rate: 1.0 mL/min.
  injection volume: 10 μL
  detecting wavelength: 215 nm
  column temperature: 30° C.

Example 3 (Recollection of ADL from AMBA-ADL and Production of Lacosamide)

AMBA-ADL (5.00 g, 13.1 mmol) was mixed with purified water (15.0 mL) and 2 mol/L hydrochloric acid (6.10 g, 11.8 mmol) was dropped into the mixed solution at the room temperature and stirred. The precipitated crystal was filtered and washed with purified water (4.10 mL) to obtain white solid-form ADL (1.77 g, yield of 78%, chemical purity of 85.6 area %). Furthermore, lacosamide (2.65 g, yield of 81%, chemical purity of 99.8 area %, diastereomeric excess of 100% de) was obtained from the recollected filtrate through acetylation in accordance with the method described in Example 19 of the patent publication WO2014/68333.

ADL:
  $^1$H-NMR (400 MHz, CDCl$_3$): δ 8.10 (d, J=7.9 Hz, 1H), 4.22-4.16 (m, 1H), 1.83 (s, 3H), 1.67-1.57 (m, 1H), 1.51-1.46 (m, 2H), 0.86 (dd, J=6.6 Hz, 13.7 Hz, 6H)
  Mass: m/z 174[M+H]$^+$ The chemical purity (area %) of ADL was measured by means of HPLC under the following conditions.
  column: CAPCELL PAK C18 MGIII (100 mm×3.0 mm, 3 μm)
  mobile phase A: 10 mmol/L ammonium acetate aqueous solution
  mobile phase B: acetonitrile/water=9/1 (volume ratio)
  gradient B solution concentration: (10/0 min.)→(90/15 min.)→(90/20 min.)
  flow rate: 0.50 mL/min.
  injection volume: 3 μL
  detecting wavelength: 215 nm
  column temperature: 40° C.

The diastereomeric excess of ADL was measured by means of HPLC under the following conditions.
  column: Chiralcel OD-H (250 mm×4.6 mm, 5 μm)
  mobile phase A: n-hexane
  mobile phase B: isopropanol
  isocratic condition for mobile phase A/B=75/25 (volume ratio)
  flow rate: 0.7 mL/min.
  injection volume: 5 μL
  detecting wavelength: 210 nm
  column temperature: 30° C.

In Examples 3 and 4, the chemical purity (area %) of lacosamide was measured by means of HPLC under the following conditions.
  column: CAPCELL PAK C18 MGIII (100 mm×3.0 mm, 3 μm)
  mobile phase A: 10 mmol/L ammonium acetate aqueous solution mobile phase B: acetonitrile/water=9/1 (volume ratio)
gradient B solution concentration: (10/0 min.)→(90/15 min.)→(90/20 min.)
flow rate: 0.50 mL/min.
injection volume: 3 μL
detecting wavelength: 215 nm
column temperature: 40° C.

The diastereomeric excess (% de) of lacosamide was measure by means of HPLC under the following conditions.
column: Chiralcel OD-H (250 mm×4.6 mm, 5 μm)
mobile phase A: n-hexane solution
mobile phase B: IPA
isocratic condition for mobile phase A/B=75/25 (volume ratio)
flow rate: 0.7 mL/min.
injection volume: 5 μL
detecting wavelength: 210 nm
column temperature: 30° C.

Example 4 (Producing Lacosamide)

AMBA-ADL (0.229 g, 0.60 mmol) was mixed with sodium hydrogencarbonate (0.101 g, 1.20 mmol) and acetic anhydride (0.112 g, 0.66 mmol) in a 20% sodium chloride solution (4.6 mL), and stirred at the room temperature (25° C.). The precipitated crystal was filtered and wished to obtain lacosamide (0.126 g, yield of 84%, chemical purity of 99.5 area %). In this Example, lacosamide was obtained by directly acetylating the R-configuration salt.

Example 5 (Production of AMBA-ADL)

The material AMBA (1.50 g, 7.21 mmol) was mixed with the resolving reagent ADL (1.19 g, 6.85 mmol) in the solvent AcOiPr (15 mL) in the presence of the aldehyde compound 5-NSA (120 mg, 0.72 mmol), and the mixture was stirred for 41 hours at 50° C. In relation to providing ADL, 50% of the total amount was provided at the initial stage of the reaction and the remaining was dividedly provided in separated three times. The reacting liquid was cooled to 5° C. and then the precipitated crystal was recollected. The recollected crystal was washed with cool AcOiPr (1 mL) of the temperature of about 5° C. to obtain the AMBA-ADL crystal (2.30 g, yield of 84%, yield of R-configuration salt per resolving reagent of 1 MR of 87.8%, chemical purity=99.8 area %, diastereomeric excess=99.5% de).

Comparative Example 2 (Producing AMBA-ADL)

The material AMBA (0.1 g, 0.48 mmol) was mixed with ADL (0.08 g, 0.46 mmol) in the solvent AcOiPr (0.7 mL) in the presence of the aldehyde compound 5-NSA (4 mg, 0.02 mmol), and the mixture was stirred for 14 hours at 65° C. The reacting liquid was cooled to 40° C. and the precipitated crystal was recollected. The recollected crystal was washed with AcOiPr (1 mL) of the room temperature to obtain the crystal AMBA-ADL (0.12 g, yield of 65.5%, yield of R-configuration salt per resolving reagent of 1 MR of 68.6%, diastereomeric excess=99<% de). As compared with Example 5, the reaction temperature was higher and the yield was lower.

Comparative Example 3 (Production of AMBA-ADL)

A mixture was prepared likewise Comparative Example 2 except for the usage amount of AcOiPr being 1 mL and being stirred under the stirring condition of for 8 hours at 80° C. The reacting liquid was cooled to the room temperature and the precipitated crystal was recollected. The recollected crystal was washed with AcOiPr (1 mL) of the room temperature to obtain the crystal AMBA-ADL (0.10 g, yield of 56.3%, yield of R-configuration salt per resolving reagent of 1 MR of 59.0%, diastereomeric excess=99<% de). As compared with Example 5, the reaction temperature was higher and the yield was lower.

The reaction conditions and the results of Example 5 and Comparative Example 3 are collectively shown in Table 2. The amount of the resolving reagent is represented by the molar ratio (MR) of the usage amount (mol) of the resolving reagent to the usage amount (mol) of AMBA. The amount of the solvent is represented by a ratio (VR) of the usage amount (mL) of the solvent to the usage amount (g) of the AMBA.

TABLE 2

| ITEMS | | EXAMPLE 5 | COMPARATIVE EXAMPLE 3 |
|---|---|---|---|
| RESOLVING REAGENT | TYPE | ADL | |
| | AMOUNT (MR) | 0.95 | |
| | PROVIDING MANNER | DIVISIONAL PROVIDING | OVERALL PROVIDING |
| SOLVENT | TYPE | AcOiPr | |
| | AMOUNT (VR) | 10 | |
| RACEMIZING REAGENT | | 5-NSA | |
| REACTION TEMPERATURE (° C.) | | 50 | 80 |
| YIELD (%) | | 84 | 56 |
| YIELD OF R-CONFIGURATION SALT PER RESOLVING REAGENT OF 1 MR (%) | | 87.8 | 59.0 |
| CHEMICAL PURITY (AREA %) | | 99.8 | — |
| DIASTEREOMERIC EXCESS (% de) | | 99.5 | 99 |

Example 6 (Production of AMBA-FLL)

[Formula 13]

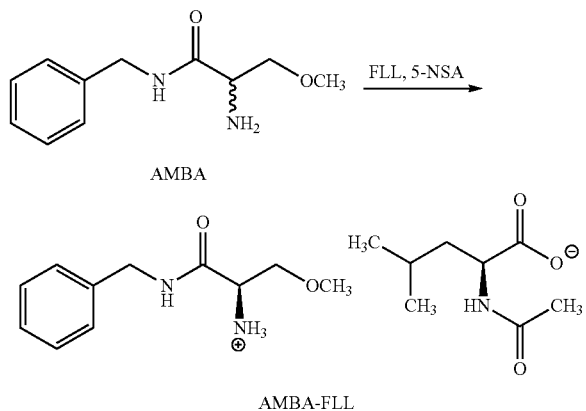

The material AMBA (0.50 g, 2.40 mmol) was mixed with the resolving reagent FLL (0.34 g, 2.16 mmol) in the solvent AcOiPr (10.0 mL) in the presence of the aldehyde compound 5-NSA (41 mg, 0.25 mmol), and the mixture was stirred for 26 hours at 50° C. In relation to providing FLL, 50% of the total amount was provided at the initial stage of the reaction and the remaining was dividedly provided in separated twice. The reacting liquid was cooled to 8° C. and the precipitated crystal was recollected. The recollected crystal was washed with cool AcOiPr (1.0 mL) in the temperature of 5° C. to obtain the AMBA-FLL crystal (0.71 g, yield of 80%, the yield of R-configuration salt per resolving reagent of 1 MR of 87.2%, chemical purity=99.6 area %, diastereomeric excess=96.2% de). Divisional providing of the resolving reagent made the reaction to highly efficiently proceed at a relatively low temperature to obtain a salt high in chemical purity and also enantiometric excess at a high yield even if a co-solvent is not used.

$^1$H-NMR (400 MHz, DMSO-d6): δ 8.67 (t, J=5.8 Hz, 1H), 8.13 (d, J=8.1 Hz, 1H), 8.00 (d, J=1.0, 1H), 7.34-7.21 (m, 5H) 4.33-4.30 (m, 2H), 4.19-4.16 (m, 1H), 3.64 (t, J=5.5, 1H), 3.53-3.52 (m, 2H), 3.26 (5, 3H), 1.64-1.41 (m, 3H), 0.86 (dd, J=6.5 Hz, 10.5 Hz, 6H)

melting point: 149° C.

The powder X-ray diffraction pattern of the obtained crystalline AMBA-FLL was measured with an X-ray Diffractometers XRD-6000 (product of Shimadzu Corporation) under the following conditions.

X-ray source: CuKα tube voltage: 40.0 kV tune electric current: 40.0 mA divergence: 1.00 deg scattering: 1.00 deg receiving: 0.15 mm mode: continuous scanning driving axis: 2θ/θ data range: 2θ=2 to 40 deg step: 0.02 deg scanning velocity: 2 deg/min.

The obtained powder X-ray diffraction pattern is shown in Table 3 and FIG. 2.

TABLE 3

| 2θ (°) | RELATIVE INTENSITY |
|---|---|
| 4.9 | 100 |
| 9.4 | 42 |
| 12.4 | 56 |
| 14.3 | 10 |
| 15.8 | 5 |
| 17.7 | 22 |
| 18.0 | 9 |
| 18.7 | 53 |
| 19.2 | 22 |
| 19.5 | 14 |
| 19.9 | 9 |
| 20.7 | 14 |
| 22.1 | 11 |
| 23.6 | 9 |
| 24.0 | 9 |
| 24.4 | 17 |
| 24.9 | 20 |
| 26.9 | 20 |
| 28.3 | 9 |
| 29.1 | 5 |
| 31.7 | 7 |
| 32.2 | 5 |
| 33.7 | 8 |
| 34.5 | 4 |
| 35.1 | 4 |
| 37.7 | 3 |

The reaction conditions and the results of Example 6 and Comparative Example 1 are collectively shown in Table 4.

TABLE 4

| ITEMS | | EXAMPLE 6 | COMPARATIVE EXAMPLE 1 |
|---|---|---|---|
| RESOLVING REAGENT | TYPE | FLL | |
| | AMOUNT (MR) | 0.9 | 1 |
| | PROVIDING MANNER | DIVISIONAL PROVIDING | OVERALL PROVIDING |
| SOLVENT | TYPE | AcOiPr | AcOiPr/IPA |
| | AMOUNT (VR) | 20 | 21 (20/1) |
| RACEMIZING REAGENT | | 5-NSA | |
| REACTION TEMPERATURE (° C.) | | 50 | 65 |
| YIELD (%) | | 80 | 77 |
| YIELD OF R-CONFIGURATION SALT PER RESOLVING REAGENT OF 1 MR (%) | | 87.2 | 73.4 |
| CHEMICAL PURITY (AREA %) | | 99.6 | 99.6 |
| DIASTEREOMERIC EXCESS (% de) | | 96.2 | 89.7 |

Example 7 (Production of AMBA-ADV)

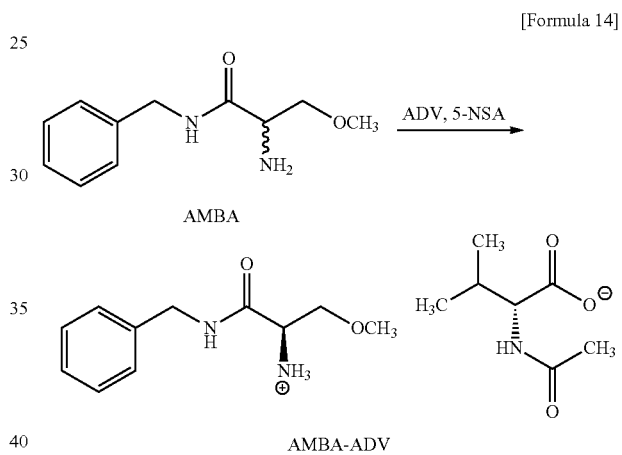

[Formula 14]

A mixture was prepared likewise Example 6 except for the resolving reagent being ADV (0.34 g, 2.16 mmol) in place of FLL and the mixture was stirred for 33 hours. In relation to providing ADV, 50% of the total amount was provided at the initial stage of the reaction and the remaining was dividedly provided in separated twice. The reacting liquid was cooled to 5° C. and then precipitated crystal was recollected. The recollected crystal was washed likewise Example 6 to obtain the crystal of AMBA-ADV (salt of (R) N-benzyl-2-amino-3-methoxypropionamide and N-acetyl-D-valine) (0.72 g, yield of 81%, yield of R-configuration salt per resolving reagent of 1 MR of 86.6%, chemical purity=99.7 area %, diastereomeric excess=92.1% de). Divisional providing of the resolving reagent made the reaction to highly efficiently proceed at a relatively low temperature to obtain a salt high in chemical purity and also enantiometric excess at a high yield even if a co-solvent is not used.

$^1$H-NMR (400 MHz, DMSO-d6): δ 8.69-8.66 (m, 1H), 7.81 (d, J=8.7 Hz, 1H), 7.34-7.21 (m, 5H), 4.82 (m, 1H), 4.32-4.27 (m, 2H), 4.09-4.05 (m, 1H), 3.66-3.52 (m, 2H), 3.26 (s, 3H), 2.08-1.96 (m, 3H), 1.87 (s, 3H), 0.85 (s, 3H), 0.84 (s, 3H)

The power X-ray diffraction patterns of the crystal obtained AMBA-ADV were measured under the same condition as that of Example 6. The obtained X-ray diffraction patterns are shown in Table 5 and FIG. 3.

TABLE 5

| 2θ (°) | RELATIVE INTENSITY |
|---|---|
| 7.0 | 100 |
| 11.6 | 8 |
| 13.8 | 4 |
| 14.8 | 33 |
| 16.7 | 6 |
| 17.4 | 4 |
| 18.0 | 21 |
| 18.7 | 28 |
| 20.0 | 7 |
| 21.9 | 37 |
| 22.9 | 10 |
| 23.3 | 7 |
| 23.9 | 9 |
| 24.6 | 21 |
| 26.1 | 25 |
| 27.8 | 8 |
| 28.6 | 4 |
| 32.5 | 6 |
| 33.8 | 4 |
| 34.8 | 5 |

Example 8 (Production of AMBA-FLA)

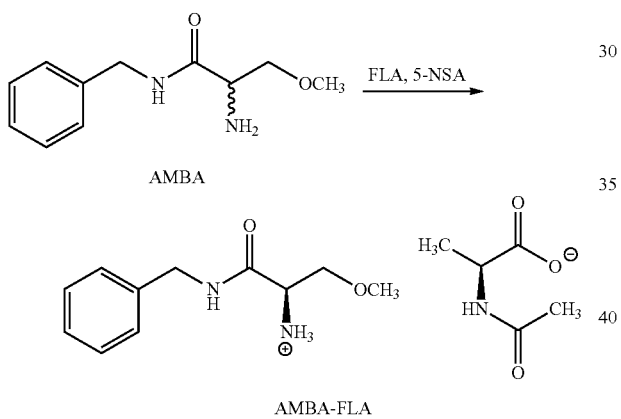

[Formula 15]

A mixture was prepared likewise Example 6 except for the resolving reagent being FLA (0.25 g, 2.16 mmol) in place of FLL and the mixture was stirred for 38 hours. In relation to providing FLA, 50% of the total amount was provided at the initial state of the reaction and the remaining was dividedly provided in separated twice. The reacting liquid was cooled to 5° C. and then the precipitated crystal was recollected. The recollected crystal was washed likewise Example 6 to obtain the crystal of AMBA-FLA (salt (R) N-benzyl-2-amino-3-methoxypropionamide and N-formyl-L-alanine (0.61 g, yield of 78%, the yield of R-configuration salt per resolving reagent of 1 MR of 81.0%, chemical purity=98.8 area %, diastereomeric excess=88.2% de). Divisional providing of the resolving reagent made the reaction to highly efficiently proceed at a relatively low temperature to obtain a salt high in chemical purity and also enantiometric excess at a high yield even if a co-solvent is not used.

$^1$H-NMR (400 MHz, DMSO-d6): δ 8.85 (t, J=5.8 Hz, 1H), 8.08 (d, J=6.8 Hz, 1H), 7.96 (s, 1H), 7.34-7.21 (m, 5H), 4.32-4.27 (m, 2H), 4.15-4.08 (m, 1H), 3.79 (t, J=5.1 Hz, 1H), 3.59 (d, J=5.1 Hz, 2H), 3.27 (s, 3H), 1.23 (d, J=7.1 Hz, 3H)

The powder X-ray diffraction pattern of the obtained crystalline AMBA-FLA was measured with an X-ray Diffractometers XRD-6100 (product of Shimadzu Corporation) under the following conditions.
X-ray source: CuKα
tube voltage: 40.0 kV
tube electric current: 40.0 mA
divergence: 1.00 deg
scattering: 1.00 deg
receiving: 0.15 mm
mode: continuous scanning
driving axis: 2θ/θ
data range: 2θ=2 to 40 deg
step: 0.02 deg
scanning velocity: 2 deg/min.

The obtained powder X-ray diffraction pattern is shown in Table 6 and FIG. 4

TABLE 6

| 2θ (°) | RELATIVE INTENSITY |
|---|---|
| 6.1 | 61 |
| 9.9 | 62 |
| 10.4 | 7 |
| 12.0 | 32 |
| 12.6 | 6 |
| 13.8 | 43 |
| 15.4 | 26 |
| 17.8 | 100 |
| 18.6 | 22 |
| 19.8 | 70 |
| 22.4 | 84 |
| 23.0 | 69 |
| 24.0 | 68 |
| 25.3 | 41 |
| 26.1 | 49 |
| 27.9 | 22 |
| 28.6 | 7 |
| 29.6 | 13 |
| 30.3 | 12 |
| 31.4 | 14 |
| 32.4 | 6 |
| 32.9 | 6 |
| 33.9 | 13 |
| 34.5 | 6 |
| 35.5 | 17 |
| 36.7 | 10 |
| 37.6 | 13 |
| 39.2 | 4 |

Hereinafter, description will now be made in relation to Comparative Examples 4-9 that attempted isomerization-crystallization using resolving reagent different from N-acetylamino acid and N-formylamino acid. In Comparative Examples 4-9, the chemical purities (area %) were measured by means of HPLC under the following conditions.
column: CAPCELL PAK C18 MGIII (100 mm×3.0 mm, 3 μm) mobile phase A: 10 mmol/L ammonium acetate aqueous solution
mobile phase B: acetonitrile/water=9/1 (volume ratio)
gradient B solution concentration: (10/0 min.)→(90/15 min.)→(90/20 min.)
flow rate: 0.50 mL/min.
injection volume: 3 μL
detecting wavelength: 215 nm
column temperature: 40° C.

The diastereomeric excesses (% de) were measured by means of HPLC under the following conditions.
column: Chiralcel OJ-H (250 mm×4.6 mm, 5 μm)

mobile phase A: n-hexane solution containing 0.1% diethylamine (vol %)
mobile phase B: ethanol
isocratic condition for mobile phase A/B=95/5 (volume ratio)
flow rate: 1.0 mL/min.
injection volume: 10 μL
detecting wavelength: 215 nm
column temperature: 30° C.

Comparative Example 4

The material AMBA (1.04 g, 5.00 mmol) was mixed with the resolving reagent (+)-DPTTA ((+)-Di-p-toluoyl-D-tartaric acid) (2.03 g, 5.25 mmol) in the solvent AcOiPr (31.2 mL) and the mixture was stirred in 0.1 hours at the room temperature. The precipitated solid was recollected under the room temperature and was washed with AcOiPr (1.0 mL) of the room temperature to obtain powder of the salt of (R) N-benzyl-2-amino-3-methoxypropionamide and (+)-DPTTA (2.88 g, yield of 97%, the yield of R-configuration salt per resolving reagent of 1 MR of 45.7%, diastereomeric excess=−0.8% de). The yield of the R-configuration salt per the resolving reagent of 1 MR was low and the obtained salt was low in diastereomeric excess.

Comparative Example 5

The material AMBA (0.25 g, 1.21 mmol) was mixed with the resolving reagent (+)-DBTA ((+)-dibenzoyl-D-tartaric acid).$H_2O$ (0.43 g, 1.15 mmol) in the solvent of AcOiPr (3.3 mL) and IPA (1.7 mL) in the presence of the aldehyde compound SA (7 mg, 0.06 mmol), and the mixture was stirred for 17 hours at 80° C. The precipitated solid was recollected under the condition of 80° C. and washed with AcOiPr (1 mL) of the room temperature to obtain the powder of the salt of (R) N-benzyl-2-amino-3-methoxypropionamide and (+)-DBTA (0.34 g, yield of 50%, diastereomeric excess=49.8% de, the yield of R-configuration salt per resolving reagent of 1 MR of 39.1%). The yield of the R-configuration salt per the resolving reagent of 1 MR was low and the obtained salt was low in diastereomeric excess.

Comparative Example 6

The material AMBA (0.10 g, 0.48 mmol) was mixed with the resolving reagent L-pyroglutamic acid (0.06 g, 0.48 mmol) in the solvent AcOiPr (1.0 mL) and the mixture was stirred 0.1 hours at 80° C. The precipitated solid was recollected under the condition of 80° C. and the solid was washed with AcOiPr (1.0 mL) of the room temperature to obtain brown solid having a high viscosity (diastereomeric excess=1.4% de).

Comparative Example 7

The mixture was prepared and stirred likewise Comparative Example 6 except for using N-Boc-L-valine (0.10 g, 0.48 mmol) in place of L-pyroglutamic acid as the resolving reagent, resulting in precipitating no crystal.

Comparative Example 8

The mixture was prepared and stirred likewise Comparative Example 6 except for using N-Boc-L-proline (0.10 g, 0.48 mmol) in place of L-pyroglutamic acid as the resolving reagent, resulting in precipitating no crystal.

Comparative Example 9

The mixture was prepared and stirred likewise Comparative Example 6 except for using 2-chloro-L-mandelic acid (0.09 g, 0.48 mmol) in place of L-pyroglutamic acid as the resolving reagent, resulting in precipitating no crystal.

INDUSTRIAL APPLICABILITY

The method of the present invention can industrially and safely producing lacosamide high in diastereomeric excess and chemical purity at a high yield and a low cost.

What is claimed is:

1. A method for producing lacosamide comprising:
   an isomerization-crystallization process that causes racemic N-benzyl-2-amino-3-methoxypropionamide to react with a resolving reagent of at least one selected from a group consisting of
      N-acetylamino acid selected from the group consisting of N-acetyl-D-leucine, N-acetyl-D-valine, N-acetyl-D-alanine, and N-acetyl-D-phenylalanine, and
      N-formylamino acid selected from the group consisting of N-formyl-L-leucine, N-formyl-L-alanine, and N-formyl-L-phenylalanine
   in a solvent in the presence of an aldehyde compound at a temperature lower than 60° C. to selectively crystallize a salt of R-configuration of N-benzyl-2-amino-3-methoxypropionamide and N-acetylamino acid or N-formylamino acid; and
   an acetylation process that acetylates the R-configuration N-benzyl-2-amino-3-methoxypropionamide contained in the salt to obtain lacosamide.

2. The method according to claim 1, wherein, in the isomerization-crystallization process, the resolving reagent is dividedly provided.

3. The method according to claim 1, wherein the acetylation process comprises:
   (i) causing the salt obtained through the isomerization-crystallization process with an acetylating reagent; or
   (ii) causing the salt obtained through the isomerization-crystallization process with an acid and causing the obtained R-configuration N-benzyl-2-amino-3-methoxypropionamide to react with the acetylating reagent.

4. The method according to claim 1, further comprising, an amination process that aminates a compound expressed by a Formula (4) to obtain the racemic N-benzyl-2-amino-3-methoxypropionamide, the amination process being carried out before the isomerization-crystallization process

[Formula 1]

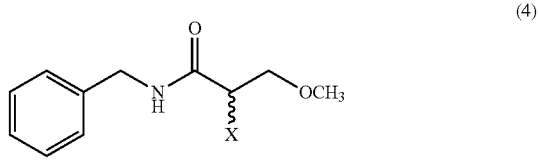

(4)

(where, X represents a leaving group).

5. A method for producing lacosamide comprising:
an isomerization-crystallization process that causes racemic N-benzyl-2-amino-3-methoxypropionamide to react with a resolving reagent of at least one selected from a group consisting of
N-acetylamino acid selected from the group consisting of N-acetyl-D-leucine, N-acetyl-D-valine, N-acetyl-D-alanine, and N-acetyl-D-phenylalanine
in a solvent in the presence of an aldehyde compound at a temperature 60° C. or less to selectively crystalize a salt of R-configuration of N-benzyl-2-amino-3-methoxypropionamide and N-acetylamino acid; and
an acetylation process that acetylates the R-configuration N-benzyl-2-amino-3-methoxypropionamide contained in the salt to obtain lacosamide.

6. The method according to claim 2, wherein the yield of an R-configuration salt per the resolving reagent of 1MR is 81.0% or more.

7. The method according to claim 1, wherein the acetylation process comprises:
(i) causing the salt obtained through the isomerization-crystallization process with an acetylating reagent in a solvent consisting of a mixed solvent of ethyl acetate and water, simple water, or an aqueous solution containing water at the concentration of 95 vol % or more in a presence of a base; or
(ii) causing the salt obtained through the isomerization-crystallization process with an acid and causing the obtained R-configuration N-benzyl-2-amino-3-methoxypropionamide to react with the acetylating reagent.

* * * * *